United States Patent
Mi et al.

(10) Patent No.: US 8,153,580 B2
(45) Date of Patent: Apr. 10, 2012

(54) NOGO RECEPTOR BINDING PROTEIN

(75) Inventors: Sha Mi, Belmont, MA (US); John McCoy, Reading, MA (US); R. Blake Pepinsky, Arlington, MA (US); Daniel H. S. Lee, Sudbury, MA (US)

(73) Assignee: Biogen Idec MA Inc., Cambridge, MA (US)

( * ) Notice: Subject to any disclaimer, the term of this patent is extended or adjusted under 35 U.S.C. 154(b) by 99 days.

(21) Appl. No.: 12/698,935

(22) Filed: Feb. 2, 2010

(65) Prior Publication Data

US 2010/0204304 A1    Aug. 12, 2010

Related U.S. Application Data

(62) Division of application No. 10/553,685, filed as application No. PCT/US2004/008323 on Mar. 17, 2004, now Pat. No. 7,785,829.

(60) Provisional application No. 60/455,756, filed on Mar. 19, 2003, provisional application No. 60/480,241, filed on Jun. 20, 2003, provisional application No. 60/492,057, filed on Aug. 1, 2003.

(51) Int. Cl.
*C07K 14/00* (2006.01)
*A61K 48/00* (2006.01)

(52) U.S. Cl. .............................. 514/1; 514/44
(58) Field of Classification Search .................. 514/1, 44
See application file for complete search history.

(56) References Cited

U.S. PATENT DOCUMENTS

| 2009/0252748 A1 | 10/2009 | Mi et al. |
| 2010/0015131 A1 | 1/2010 | Mi et al. |
| 2010/0074907 A1 | 3/2010 | Mi et al. |
| 2010/0297121 A1 | 11/2010 | Mi |

OTHER PUBLICATIONS

Co-pending Application, U.S. Appl. No. 13/158,307 inventors Mi, et al., filed on Jun. 10, 2010.
Co-pending Application, U.S. Appl. No. 13/243,795 inventors Mi, et al., filed on Sep. 23, 2011.
Lehner, B., et al., "How to use RNA interference," *Briefings in Functional Genomics and Proteomics* 3(1):68-83, Henry Stewart Publications, England (Apr. 2004).
Dousset, V., et al. "Lysolecithin-Induced Demyelination in Primates: Preliminary In Vivo Study with MR and Magnetization Transfer," *American Journal of Neuroradiology* 16:225-231, American Society of Neroradiology, United States (Feb. 1995).
Office Action mailed Jun. 24, 2011 in U.S. Appl. No. 12/092,662, Mi, et al., filed Sep. 26, 2008.
Response to Office Action filed Oct. 31, 2011 in U.S. Appl. No. 12/092,662, Mi, et al., filed Sep. 26, 2008.

*Primary Examiner* — Karen Carlson
(74) *Attorney, Agent, or Firm* — Sterne, Kessler, Goldstein & Fox PLLC

(57) ABSTRACT

The invention provides Sp35 polypeptides and fusion proteins thereof, Sp35 antibodies and antigen-binding fragments thereof and nucleic acids encoding the same. The invention also provides compositions comprising, and methods for making and using, such Sp35 antibodies, antigen-binding fragments thereof, Sp35 polypeptides and fusion proteins thereof.

16 Claims, 9 Drawing Sheets

FIG. 1

GGAGAGACATGCGATTGGTGACCGAGCCGAGCGGACCGAAGGCGCGCCCGA
GATGCAGGTGAGCAAGAGGATGCTGGCGGGGGGCGTGAGGAGCATGCCCAG
CCCCCTCCTGGCCTGCTGGCAGCCCATCCTCCTGCTGGTGCTGGGCTCAGTGC
TGTCAGGCTCGGCCACGGGCTGCCCGCCCCGCTGCGAGTGCTCCGCCCAGGA
CCGCGCTGTGCTGTGCCACCGCAAGCGCTTTGTGGCAGTCCCCGAGGGCATC
CCCACCGAGACGCGCCTGCTGGACCTAGGCAAGAACCGCATCAAAACGCTCA
ACCAGGACGAGTTCGCCAGCTTCCCGCACCTGGAGGAGCTGGAGCTCAACGA
GAACATCGTGAGCGCCGTGGAGCCCGGCGCCTTCAACAACCTCTTCAACCTC
CGGACGCTGGGTCTCCGCAGCAACCGCCTGAAGCTCATCCCGCTAGGCGTCT
TCACTGGCCTCAGCAACCTGACCAAGCTGGACATCAGCGAGAACAAGATTGT
TATCCTACTGGACTACATGTTTCAGGACCTGTACAACCTCAAGTCACTGGAGG
TTGGCGACAATGACCTCGTCTACATCTCTCACCGCGCCTTCAGCGGCCTCAAC
AGCCTGGAGCAGCTGACGCTGGAGAAATGCAACCTGACCTCCATCCCCACCG
AGGCGCTGTCCCACCTGCACGGCCTCATCGTCCTGAGGCTCCGGCACCTCAA
CATCAATGCCATCCGGGACTACTCCTTCAAGAGGCTCTACCGACTCAAGGTCT
TGGAGATCTCCCACTGGCCCTACTTGGACACCATGACACCCAACTGCCTCTAC
GGCCTCAACCTGACGTCCCTGTCCATCACACACTGCAATCTGACCGCTGTGCC
CTACCTGGCCGTCCGCCACCTAGTCTATCTCCGCTTCCTCAACCTCTCCTACA
ACCCCATCAGCACCATTGAGGGCTCCATGTTGCATGAGCTGCTCCGGCTGCA
GGAGATCCAGCTGGTGGGCGGGCAGCTGGCCGTGGTGGAGCCCTATGCCTTC
CGCGGCCTCAACTACCTGCGCGTGCTCAATGTCTCTGGCAACCAGCTGACCA
CACTGGAGGAATCAGTCTTCCACTCGGTGGGCAACCTGGAGACACTCATCCT
GGACTCCAACCCGCTGGCCTGCGACTGTCGGCTCCTGTGGGTGTTCCGGCGCC
GCTGGCGGCTCAACTTCAACCGGCAGCAGCCCACGTGCGCCACGCCCGAGTT
TGTCCAGGGCAAGGAGTTCAAGGACTTCCCTGATGTGCTACTGCCCAACTACT
TCACCTGCCGCCGCGCCCGCATCCGGGACCGCAAGGCCCAGCAGGTGTTTGT
GGACGAGGGCCACACGGTGCAGTTTGTGTGCCGGGCCGATGGCGACCCGCCG
CCCGCCATCCTCTGGCTCTCACCCCGAAAGCACCTGGTCTCAGCCAAGAGCA
ATGGGCGGCTCACAGTCTTCCCTGATGGCACGCTGGAGGTGCGCTACGCCCA
GGTACAGGACAACGGCACGTACCTGTGCATCGCGGCCAACGCGGGCGGCAA
CGACTCCATGCCCGCCCACCTGCATGTGCGCAGCTACTCGCCCGACTGGCCCC
ATCAGCCCAACAAGACCTTCGCTTTCATCTCCAACCAGCCGGGCGAGGGAGA
GGCCAACAGCACCCGCGCCACTGTGCCTTTCCCCTTCGACATCAAGACCCTCA
TCATCGCCACCACCATGGGCTTCATCTCTTTCCTGGGCGTCGTCCTCTTCTGCC
TGGTGCTGCTGTTTCTCTGGAGCCGGGGCAAGGGCAACACAAAGCACAACAT
CGAGATCGAGTATGTGCCCCGAAAGTCGGACGCAGGCATCAGCTCCGCCGAC
GCGCCCCGCAAGTTCAACATGAAGATGATATGAGGCCGGGGCGGGGGGCAG
GGACCCCCGGGCGGCCGGGCAGGGGAAGGGGCCTGGCCGCCACCTGCTCACT
CTCCAGTCCTTCCCACCTCCTCCCTACCCTTCTACACACGTTCTCTTTCTCCCT
CCCGCCTCCGTCCCCTGCTGCCCCCGCCAGCCCTCACCACCTGCCCTCCTTC
TACCAGGACCTCAGAAGCCCAGACCTGGGGACCCCACCTACACAGGGGCATT
GACAGACTGGAGTTGAAAGCCGACGAACCGACACGCGGCAGAGTCAATAAT
TCAATAAAAAAGTTACGAACTTTCTCTGTAACTTGGGTTTCAATAATTATGGA
TTTTTATGAAAACTTGAAATAATAAAAGAGAAAAAAACTATTTCCTATAGC

FIG. 1 (continued)

TAGTCGGAATGCAAACTTTTGACGTCCTGATTGCTCCAGGGCCCTCTTCCAAC
TCAGTTTCTTGTTTTTCTCTTCNTCCTNCTCCTCTTCTTCCTCCTTTCTCTTCTCT
TCCCCCAGTGGGGAGGGATCACTCAGGAAAACAGGAAAGGAGGTTCCAGCC
CCACCCACCTGCCCACCCCGCCCCAGGCACCATCAGGAGCAGGCTAGGGGGC
AGGCCTGGGCCCAGCTCCGGGCTGGCTTTTTGCAGGGCGCAGGTGGAGGGGA
CAGGTCTGCCGATGGGGGTGGGAGCCTGTCTGCTGGGCTGCCAGGCGGCACC
ACTGCAAGGGGTGGGAGCCTGGCTCGGGTGTGGCTGAGACTCTGGACAGAGG
CTGGGGTCCTCCTGGGGGACAGCACAGTCAGTGGAGAGAGCCAGGGGCTGG
AGGTGGGGCCCACCCCAGCCTCTGGTCCAGCTCTGCTGCTCACTTGCTGTGT
GGCCCTCAAGCAGGTCCACTGGCCTCTCTGGGCCTCAGTCTCCACATCTGTAC
AAATGGGAACATTACCCCCTGCCCTGCCTACCTNANAGGGCTGTTNTGAGGN
ATNGATGAGATGATGTATGT

FIG. 2

```
MLAGGVRSMPSPLLACWQPILLLVLGSVL
SGSATGCPPRCECSAQDRAVLCHRKRFVA
VPEGIPTETRLLDLGKNRIKTLNQDEFASF
PHLEELENEIVSAVEPGAFNNLFNLRTL
GLRSNRLKLIPLGVFTGLSNLTKLDISENKI
VILLDYMFQDLYNLKSLEVGDNDLVISHR
AFSGLNSLEQLTEKCNLTSIPTEALSHLH
GLIVLRLRHLNINAIRDYSFKRLYRLKVLEI
SHWPYLDTMTPNCLYGLNLTSLSITHCNLT
AVPYLAVRHLVYLRFLNSYNPISTIEGSM
LHELLRLQEIQLVGGQLAVVEPYAFRGLNY
LRVLNVSGNLTTLEESVFHSVGNLETLIL
DSNPLACDCRLLWVFRRRWRLNFNRQQPT
CATPEFVQGKEFKDFPDVLLPNYFTCRRA
RIRDRKAQQVFVDEGHTVQFVCRADGDPP
PAILWLSPRKHLVSAKSNGRLTVFPDGTLE
VRYAQVQDNGTYLCIAANAGGNDSMPAHL
HVRSYSPDWPHQPNKTFAFISNQPGEGEA
NSTRATVPFPFDIKTLIIATTMGFISFLGVV
LFCLVLLFLWSRGKGNTKHNIEIEYVPRKS
DAGISSADAPRKFNMKMI
```

NOGO RECEPTOR BINDING PROTEIN

RELATED APPLICATIONS

This is a divisional of application Ser. No. 10/553,685, §371 date of Nov. 1, 2006 now U.S. Pat. No. 7,785,829, which is the National Stage of International Application No. PCT/US2004/008323, filed Mar. 17, 2004, which claims the benefit under 35 U.S.C. §119(e) to U.S. Provisional Application No. 60/455,756, filed Mar. 19, 2003; U.S. Provisional Application No. 60/480,241, filed Jun. 20, 2003; and U.S. Provisional Application No. 60/492,057, filed Aug. 1, 2003, all of which are incorporated herein by reference in their entireties.

REFERENCE TO A SEQUENCE LISTING SUBMITTED ELECTRONICALLY VIA EFS-WEB

The content of the electronically submitted sequence listing (Name: sequencelisting_ascii.txt, Size: 17,573 bytes; and Date of Creation: Feb. 2, 2010) is herein incorporated by reference in its entirety.

FIELD OF THE INVENTION

This invention relates to neurology, neurobiology and molecular biology. More particularly, this invention relates to molecules and methods for treatment of neurological diseases, disorders and injuries such as spinal cord injury.

BACKGROUND OF THE INVENTION

Axons and dendrites extend from neurons. The distal tip of an extending axon or neurite includes a specialized region, known as the growth cone. Growth cones sense the local environment and guide axonal growth toward a neuron's target cell. Growth cones respond to environmental cues, for example, surface adhesiveness, growth factors, neurotransmitters and electric fields. The growth cones generally advance at a rate of one to two millimeters per day. The growth cone explores the area ahead of it and on either side, by means of elongations classified as lamellipodia and filopodia. When an elongation contacts an unfavorable surface, it withdraws. When an elongation contacts a favorable growth surface, it continues to extend and guides the growth cone in that direction. When the growth cone reaches an appropriate target cell a synaptic connection is created.

Nerve cell function is influenced by contact between neurons and other cells in their immediate environment (Rutishauser, et al., 1988, Physiol. Rev. 68:819). These cells include specialized glial cells, oligodendrocytes in the central nervous system (CNS), and Schwann cells in the peripheral nervous system (PNS), which sheathe the neuronal axon with myelin (Lemke, 1992, in An Introduction to Molecular Neurobiology, Z. Hall, Ed., p. 281, Sinauer).

CNS neurons have the inherent potential to regenerate after injury, but they are inhibited from doing so by inhibitory proteins present in myelin (Brittis et al., 2001, Neuron 30:11-14; Jones et al, 2002, J. Neurosci. 22:2792-2803; Grimpe et al, 2002, J. Neurosci.:22:3144-3160).

Several myelin inhibitory proteins found on oligodendrocytes have been characterized. Known examples of myelin inhibitory proteins include NogoA (Chen et al., Nature, 2000, 403, 434-439; Grandpre et al., Nature 2000, 403, 439-444), myelin associated glycoprotein (MAG) (McKerracher et al., 1994, Neuron 13:805-811; Mukhopadhyay et al., 1994, Neuron 13:757-767) and oligodendrocyte glycoprotein (OM-gp), Mikol et al., 1988, J. Cell. Biol. 106:1273-1279). Each of these proteins has been separately shown to be a ligand for the neuronal NgR1 (Wang et al., Nature 2002, 417, 941-944; Grandpre et al., Nature 2000, 403, 439-444; Chen et al., Nature, 2000, 403, 434-439; Domeniconi et al., Neuron 2002, published online Jun. 28, 2002).

Nogo receptor-1 (NgR1) is a GPI-anchored membrane protein that contains 8 leucine rich repeats (Fournier et al., 2001, Nature 409:341-346). Upon interaction with inhibitory proteins (e.g., NogoA, MAG and OM-gp), the NgR1 complex transduces signals that lead to growth cone collapse and inhibition of neurite outgrowth.

There is an unmet need for molecules and methods for inhibiting NgR1-mediated growth cone collapse and the resulting inhibition of neurite outgrowth.

SUMMARY OF THE INVENTION

We have made various discoveries regarding a polypeptide designated "Sp35" (our designation). Alternate designations for Sp35 include "LINGO" and "LINGO-1." Our discoveries include the following. Sp35 binds to NgR1. Sp35 binds to itself in a homotypic interaction. An Sp35-Fc fusion protein induces or promotes fasciculation in granular neurons. An Sp35-Fc fusion protein promotes neuronal survival in both the rubro-spinal tract hemisection injury model and the optic nerve transection model. Sp35 retrovirus-infected cortical primary cells, when delivered into spinal cord-injured rats, result in enhanced neuron survival, increased β III tubulin staining of axons, and increased myelin content.

Based in part on these discoveries, the invention features an isolated nucleic acid containing a nucleotide sequence encoding a polypeptide wherein: (a) the polypeptide includes (i) an Sp35 LRR domain, (ii) an Sp35 basic region C-terminal to the LRR domain, and (iii) an Sp35 immunoglobulin (Ig) domain C-terminal to the basic region; and (b) the polypeptide lacks a transmembrane domain. The Sp35 LRR domain can contain a carboxy-terminal LRR (LRRCT), an amino-terminal LRR (LRRNT), or both. In some embodiments of the invention, the encoded Sp35 polypeptide lacks the cytoplasmic domain. In some embodiments, the encoded Sp35 polypeptide includes amino acid residues 34-532 of SEQ ID NO: 2 and lacks amino acid residues 533-614.

The invention also includes a nucleic acid encoding a polypeptide wherein the polypeptide includes an Sp35 Ig domain and lacks an Sp35 LRR domain, an Sp35 basic region, a transmembrane domain, and a cytoplasmic domain.

The invention also includes a nucleic acid encoding a polypeptide wherein the polypeptide includes an Sp35 LRR domain and lacks an Sp35 Ig domain, an Sp35 basic region, a transmembrane domain, and a cytoplasmic domain.

The invention also includes a nucleic acid encoding a polypeptide lacking a functional cytoplasmic domain but including all the other Sp35 domains. For example, the encoded polypeptide could include amino acids 1-576 of SEQ ID NO: 2 (prior to processing of the signal sequence).

In some embodiments of the invention, the encoded polypeptide is a fusion polypeptide containing a non-Sp35 moiety. The non-Sp35 moiety can be, for example, an Ig moiety, a serum albumin moiety, a targeting moiety, a reporter moiety, or a purification-facilitating moiety. A preferred non-Sp35 moiety is an Ig moiety, e.g., an Fc moiety.

The nucleotide sequence can be operatively linked to an expression control sequence, for example, in an expression vector. The invention also includes a host cell transformed with a vector that expresses an Sp35 polypeptide of the invention.

The invention also includes an Sp35 polypeptide encoded by any of the above-described nucleic acids.

The invention also includes an Sp35 polypeptide conjugated to a polymer, e.g., a polyalkylene glycol, a sugar polymer, and a polypeptide. A preferred polymer is a polyalkylene glycol, e.g., polyethylene glycol (PEG). The polypeptide can be conjugated to 1, 2, 3 or 4 polymers. Preferably, the total molecular weight of the conjugated polymers is from 20,000 Da to 40,000 Da per Sp35 polypeptide.

The invention also includes a method of inhibiting signal transduction by NgR1. The method includes contacting the NgR1 with an effective amount of an Sp35 polypeptide. Preferred polypeptides for use in the method include the following:

(a) an Sp35 polypeptide, wherein: (a) the polypeptide includes (i) an Sp35 LRR domain, (ii) an Sp35 basic region C-terminal to the LRR domain, and (iii) an Sp35 immunoglobulin (Ig) domain C-terminal to the basic region; and (b) the polypeptide lacks a transmembrane domain; and (b) an Sp35 polypeptide that includes an Sp35 Ig domain and lacks an Sp35 LRR domain, an Sp35 basic region, a transmembrane domain, and a cytoplasmic domain.

The invention also includes a method of decreasing inhibition of axonal growth of a central nervous system (CNS) neuron. The method includes contacting the neuron with an effective amount of a polypeptide such as an Sp35 polypeptide, an anti-Sp35 antibody, or an antigen-binding fragment of an anti-Sp35 antibody.

The invention also includes a method of inhibiting growth cone collapse of a CNS neuron. The method includes contacting the neuron with an effective amount of a polypeptide such as an Sp35 polypeptide, an anti-Sp35 antibody, or an antigen-binding fragment of an anti-Sp35 antibody.

The invention also includes a method of treating a CNS disease, disorder or injury in a mammal. The method includes administering to the mammal a therapeutically effective amount of a polypeptide such as an Sp35 polypeptide, an anti-Sp35 antibody, or an antigen-binding fragment of an anti-Sp35 antibody. In some embodiments of the invention, the CNS disease, disorder or injury is a spinal cord injury. The Sp35 polypeptide can be administered locally. In some embodiments of the method, the Sp 35 polypeptide is administered initially within 48 hours of a spinal cord injury. For local administration, the therapeutically effective amount of the polypeptide preferably is from 10 µg/kg to 10 mg/kg. For systemic administration, the therapeutically effective amount of the polypeptide preferably is from 1 mg/kg to 20 mg/kg.

The invention also includes an ex vivo gene therapy method of treating a CNS disease, disorder or injury in a mammal. The method includes (a) providing a cultured host cell expressing a recombinant Sp35 polypeptide; and (b) introducing the host cell into the mammal at the site of the CNS disease, disorder or injury, e.g., spinal cord injury. The cultured host cell can be derived from the mammal to be treated. In this ex vivo gene therapy method, the recombinant Sp35 polypeptide can be a full-length Sp35 polypeptide.

The invention also includes a method of promoting myelination at the site of the CNS disease, disorder or injury. The method includes contacting the site of the CNS disease, disorder or injury with an effective amount of an Sp35 polypeptide, e.g., a polypeptide containing an Sp35 LRR domain and lacking an Sp35 Ig domain, an Sp35 basic region, a transmembrane domain, and a cytoplasmic domain.

The invention also includes an in vivo gene therapy method of treating a CNS disease, disorder or injury by in vivo gene therapy. The method includes the steps of administering to a mammal, at or near the site of the disease, disorder or injury, a viral vector containing a nucleotide sequence that encodes an Sp35 polypeptide so that the Sp35 polypeptide is expressed from the nucleotide sequence in the mammal in an amount sufficient to reduce inhibition of axonal extension by neurons at or near the site of the injury. The viral vector can be, e.g., an adenoviral vector, a lentiviral vector, a baculoviral vector, an Epstein Barr viral vector, a papovaviral vector, a vaccinia viral vector, and a herpes simplex viral vector. The disease, disorder or injury can be, e.g., spinal cord injury or optic nerve injury. The viral vector can be administered by a route such as topical administration, intraocular administration, parenteral administration, intrathecal administration, subdural administration and subcutaneous administration.

The invention also includes a method of promoting survival of a neuron at risk of dying. The method includes contacting the neuron with an effective amount of an Sp35 polypeptide. The Sp35 polypeptide can be a soluble form of Sp35, e.g., an Sp35-Fc fusion protein. The neuron can be in vitro or in vivo, e.g., in a mammal with a neurodegenerative disease disorder or injury, e.g., multiple sclerosis, ALS, Huntington's disease, Alzheimer's disease, Parkinson's disease, diabetic neuropathy, stroke, traumatic brain injuries and spinal cord injury. In some embodiments of the invention, the Sp35 polypeptide is administered indirectly by: (a) providing a cultured host cell expressing a recombinant Sp35 polypeptide; and (b) introducing the host cell into the mammal at the site of the neuron. In some embodiments of the invention, the polypeptide is administered indirectly through in vivo gene therapy. In such an embodiment, the method includes administering, at or near the site of the neuron, a viral vector comprising a nucleotide sequence that encodes an Sp35 polypeptide so that the Sp35 polypeptide is expressed from the nucleotide sequence in the mammal in an amount sufficient to promote survival of the neuron.

As used herein, "full length human Sp35 polypeptide" means the polypeptide whose amino acid sequence is amino acids 34-614 of SEQ ID NO: 2.

As used herein, "heterologous moiety" means an amino acid sequence not present in a full-length Sp35 polypeptide.

As used herein, "nogo receptor-1" means the polypeptide whose sequence is publicly available under Genbank accession no. AAG53612.

As used herein, "Sp35 antagonist polypeptide" means an Sp35 polypeptide that blocks, inhibits, or interferes with the biological activity of naturally-occurring Sp35.

As used herein, "Sp35 basic region" means the following amino acid motif:

| | |
|---|---|
| R R A R I R D R K | (SEQ ID NO: 4) |
| K K V K V K E K R | (SEQ ID NO: 5) |
| R R L R L R D R K | (SEQ ID NO: 6) |
| R R G R G R D R K | (SEQ ID NO: 7) |
| R R I R A R D R K | (SEQ ID NO: 8) |

The top row of amino acids (in bold; SEQ ID NO: 4) is the preferred Sp35 basic region sequence, with variants showing optional substitutions shown below (SEQ ID NOS: 5, 6, 7 and 8).

As used herein, "Sp35 fusion protein" means a fusion protein that includes an Sp35 moiety fused to a heterologous moiety.

As used herein, "Sp35 Ig domain" means amino acids 433-493 of SEQ ID NO: 2, provided that the sequence can contain up to five individual amino acid insertions, deletions, or conservative amino acid substitutions. The following substitutions (numbering based on SEQ ID NO: 2) are expressly included: V to M at position 6; S to G at position 294; V to A at position 348; and R to H at position 419.

As used herein, "Sp35 LRR domain" means a domain that includes 10 to 14 of the leucine rich repeat sequences, including the LRRNT and LRRCT, listed in Table 1, provided that up to five amino acid insertions, deletions, or conservative amino acid substitutions can appear within the aggregate 10-14 leucine rich repeats.

As used herein, "Sp35 moiety" means a biologically active fragment of a full-length Sp35 polypeptide.

As used herein, "Sp35 polypeptide" means an Sp35 moiety or a fusion protein that includes an Sp35 moiety.

Unless otherwise defined, all technical and scientific terms used herein have the same meaning as commonly understood by one of ordinary skill in the art to which the invention pertains. In case of conflict, the present specification, including definitions, will control. All publications, patents and other references mentioned herein are incorporated by reference.

Although methods and materials similar or equivalent to those described herein can be used in the practice or testing of the invention, the preferred methods and materials are described below. The materials, methods and examples are illustrative only, and are not intended to be limiting. Other features and advantages of the invention will be apparent from the detailed description and from the claims.

BRIEF DESCRIPTION OF THE DRAWINGS

FIG. 1 is the nucleotide sequence of a full-length human Sp35 cDNA (SEQ ID NO:1)

FIG. 2 is the amino acid sequence of a full-length human Sp35 polypeptide (SEQ ID NO: 2).

DETAILED DESCRIPTION OF THE INVENTION

Figure 3:
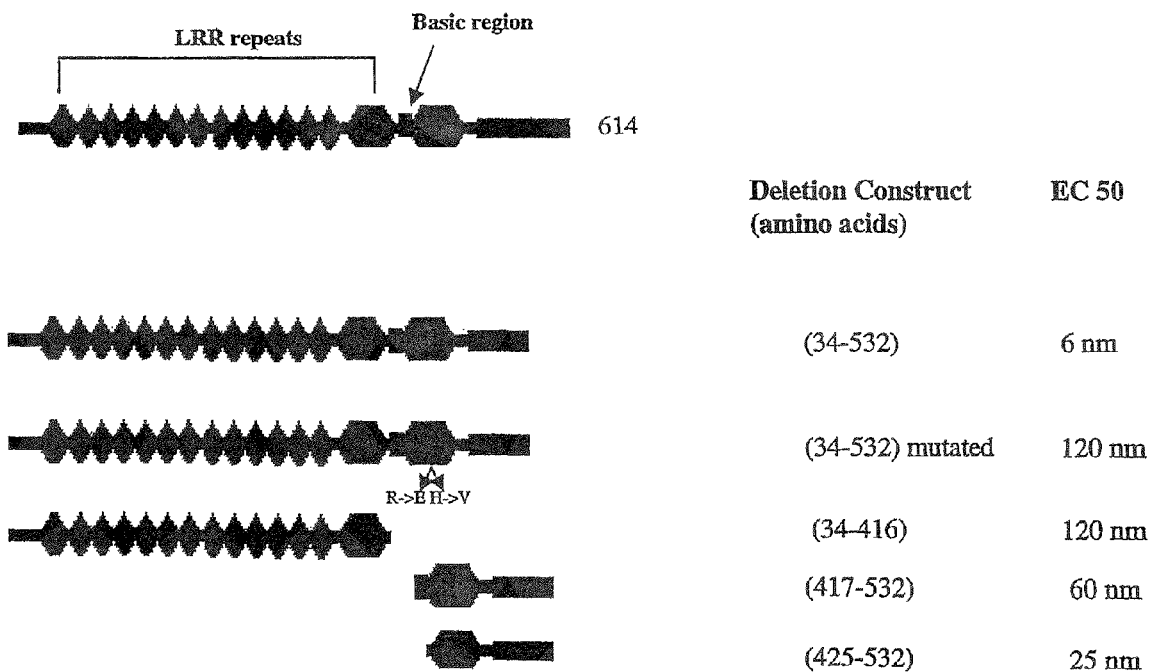
FIG. 3 is a schematic illustration of the Sp35 domain structure and deletion mapping to identify Sp35 sequence(s) that bind to NgR1.

Naturally occurring human Sp35 is a glycosylated CNS-specific protein containing 614 amino acids (FIG. 2; SEQ ID NO: 2). The human, full-length wild-type SP35 polypeptide contains an LRR domain consisting of 14 leucine-rich repeats (including N- and C-terminal caps), an Ig domain, a transmembrane region, and a cytoplasmic domain (FIG. 3). The cytoplasmic domain contains a canonical tyrosine phosphorylation site. In addition, the naturally occurring Sp35 protein contains a signal sequence, a short basic region between the LRRCT and Ig domain, and a transmembrane region between the Ig domain and the cytoplasmic domain (FIG. 3). The human Sp35 gene contains alternative translation start codons, so that six additional amino acids, i.e., MQVSKR (SEQ ID NO: 9) may or may not be present at the N-terminus of the Sp35 signal sequence. Table 1 lists the Sp35 domains and other regions, according to amino acid residue number, based on the sequence in FIG. 2 (SEQ ID NO: 2).

TABLE 1

| Domain or Region | Beginning Residue | Ending Residue |
| --- | --- | --- |
| Signal Sequence | 1 | 33 |
| LRRNT | 34 | 64 |
| LRR | 66 | 89 |
| LRR | 90 | 113 |
| LRR | 114 | 137 |
| LRR | 138 | 161 |
| LRR | 162 | 185 |
| LRR | 186 | 209 |
| LRR | 210 | 233 |
| LRR | 234 | 257 |
| LRR | 258 | 281 |
| LRR | 282 | 305 |
| LRR | 306 | 329 |
| LRR | 330 | 353 |
| LRRCT | 363 | 416 |
| Basic | 417 | 424 |
| Ig | 433 | 493 |
| Connecting sequence | 494 | 551 |
| Transmembrane | 552 | 576 |
| Cytoplasmic | 577 | 614 |

Tissue distribution and developmental expression of Sp35 has been studied in humans and rats. Sp35 biology has been studied in an experimental animal (rat) model. Expression of rat SP35 is localized to CNS neurons and brain oligodendrocytes, as determined by northern blot and immuno-histochemical staining. Rat Sp35 mRNA expression level is regulated developmentally, peaking shortly after birth, i.e., ca. postnatal day one. In a rat spinal cord transection injury model, Sp35 is up-regulated at the injury site, as determined by RT-PCR.

The inventors have discovered that full-length, wild-type Sp35 binds to NgR1. Soluble derivatives of Sp35 function as Sp35 antagonist polypeptides by binding to NgR1 and blocking, inhibiting, or interfering with its function, thereby relieving the NgR1-mediated inhibition of axonal extension that normally takes place in CNS neurons. This is beneficial in situations where axonal extension or neurite sprouting is needed in the brain or spinal cord. Spinal cord injury, including partial or complete crush or severance, exemplifies a situation in which axonal extension is needed, but is normally inhibited through operation of the Nogo pathway. Examples of diseases or disorders in which axonal extension and/or neurite sprouting in the brain would be beneficial include stroke, multiple sclerosis, and other neurodegenerative diseases or disorders.

In methods of the present invention, an Sp35 polypeptide or an Sp35 blocking antibody (or antigen-binding antibody fragment) can be administered directly as a preformed polypeptide, or indirectly through a nucleic acid vector, to antagonize NgR1 function and permit beneficial axonal outgrowth.

In some embodiments of the invention a soluble Sp35 antagonist polypeptide is administered in a treatment method that includes: (1) transforming or transfecting an implantable host cell with a nucleic acid, e.g., a vector, that expresses an Sp35 polypeptide; and (2) implanting the transformed host cell into a mammal, at the site of a disease, disorder or injury. For example, the transformed host cell can be implanted at the site of a spinal cord injury. In some embodiments of the invention, the implantable host cell is removed from a mammal, temporarily cultured, transformed or transfected with an isolated nucleic acid encoding a soluble Sp35 polypeptide, and implanted back into the same mammal from which it was removed. The cell can be, but is not required to be, removed from the same site at which it is implanted. Such embodiments, sometimes known as ex vivo gene therapy, can provide a continuous supply of the Sp35 polypeptide, localized at the site of site of action, for a limited period of time.

The invention provides oligopeptides useful as modulators of the Sp35 interaction with NgR1 and Sp35 homotypic interactions. The oligopeptides include the following amino acid motif:

| | | | | | | |
|---|---|---|---|---|---|---|
| L | S | P | R | K | H | (SEQ ID NO: 10) |
| I | T | P | K | R | R | (SEQ ID NO: 11) |
| A | C | P | H | H | K | (SEQ ID NO: 12) |
| V | S | P | R | K | H | (SEQ ID NO: 13) |

The top row of amino acids (in bold; SEQ ID NO: 10) is the preferred sequence, with variants comprising optional substitutions shown below (SEQ ID NOS: 11, 12 and 13).

Various exemplary Sp35 polypeptides, anti-Sp35 antibodies and antibody fragments, and methods and materials for obtaining these molecules for practicing the present invention are described below.

Fusion Proteins and Conjugated Polypeptides

Some embodiments of the invention involve the use of an Sp35 polypeptide, e.g., an Sp35 antagonist polypeptide, wherein an Sp35 moiety is fused to a heterologous polypeptide moiety to form an Sp35 fusion protein. Sp35 fusion proteins can be used to accomplish various objectives, e.g., increased serum half-life, improved bioavailability, in vivo targeting to a specific organ or tissue type, improved recombinant expression efficiency, improved host cell secretion, ease of purification, and higher avidity. Depending on the objective(s) to be achieved, the heterologous moiety can be inert or biologically active. Also, it can be chosen to be stably fused to the Sp35 moiety or to be cleavable, in vitro or in vivo. Heterologous moieties to accomplish different objectives are known in the art.

As an alternative to expression of a Sp35 fusion protein, a chosen heterologous moiety can be preformed and chemically conjugated to the Sp35 moiety. In most cases, a chosen heterologous moiety will function similarly, whether fused or conjugated to the Sp35 moiety. Therefore, in the following discussion of heterologous amino acid sequences, unless otherwise noted, it is to be understood that the heterologous sequence can be joined to the Sp35 moiety in the form of a fusion protein or as a chemical conjugate.

Pharmacologically active polypeptides such as Sp35 often exhibit rapid in vivo clearance, necessitating large doses to achieve therapeutically effective concentrations in the body. In addition, polypeptides smaller than about 60 kDa potentially undergo glomerular filtration, which sometimes leads to nephrotoxicity. Fusion or conjugation of relatively small polypeptides such as Sp35 fragments can be employed to reduce or avoid the risk of such nephrotoxicity. Various heterologous amino acid sequences, i.e., polypeptide moieties or "carriers," for increasing the in vivo stability, i.e., serum half-life, of therapeutic polypeptides are known.

Due to its long half-life, wide in vivo distribution, and lack of enzymatic or immunological function, essentially full-length human serum albumin (HSA), or an HSA fragment, is a preferred heterologous moiety. Through application of methods and materials such as those taught in Yeh et al., 1992, Proc. Natl. Acad. Sci. USA, 89:1904-1908 and Syed et al., 1997, Blood 89:3243-3252, HSA can be used to form an Sp35 fusion protein or conjugate that displays pharmacological activity by virtue of the Sp35 moiety while displaying significantly increased, e.g., 10-fold to 100-fold higher, in vivo stability. Preferably, the C-terminus of the HSA is fused to the N-terminus of the Sp35 moiety. Since HSA is a naturally secreted protein, the HSA signal sequence can be exploited to obtain secretion of the Sp35 fusion protein into the cell culture medium, when the fusion protein is produced in a eukaryotic, e.g., mammalian, expression system.

Some embodiments of the invention employ an Sp35 polypeptide wherein an Sp35 moiety is fused to an Fc region, i.e., the C-terminal portion of an Ig heavy chain constant region. Potential advantages of an Sp35-Fc fusion include solubility, in vivo stability, and multivalency, e.g., dimerization. The Fc region used can be an IgA, IgD, or IgG Fc region (hinge-CH2-CH3). Alternatively, it can be an IgE or IgM Fc region (hinge-CH2-CH3-CH4). An IgG Fc region is preferred, e.g., an IgG1 Fc region or IgG4 Fc region. Materials and methods for constructing and expressing DNA encoding Fc fusions are known in the art and can be applied to obtain Sp35 fusions without undue experimentation. Some embodiments of the invention employ an Sp35 fusion protein such as those described in Capon et al. U.S. Pat. Nos. 5,428,130 and 5,565,335.

The signal sequence is a polynucleotide that encodes an amino acid sequence that initiates transport of a protein across the membrane of the endoplasmic reticulum. Signal sequences useful for constructing an immunofusin include antibody light chain signal sequences, e.g., antibody 14.18 (Gillies et.al., 1989, J. Immunol. Meth., 125:191-202), antibody heavy chain signal sequences, e.g., the MOPC141 antibody heavy chain signal sequence (Sakano et al., 1980, Nature 286:5774). Alternatively, other signal sequences can be used. See, for example, Watson, 1984, Nucleic Acids Research 12:5145). The signal peptide is usually cleaved in the lumen of the endoplasmic reticulum by signal peptidases.

This results in the secretion of a immunofusin protein containing the Fc region and the Sp35 moiety.

In some embodiments the DNA sequence encodes a proteolytic cleavage site between the secretion cassette and the Sp35 moiety. A cleavage site provides for the proteolytic cleavage of the encoded fusion protein, thus separating the Fc domain from the target protein. Useful proteolytic cleavage sites include amino acids sequences recognized by proteolytic enzymes such as trypsin, plasmin, thrombin, factor Xa, or enterokinase K.

The secretion cassette can be incorporated into a replicable expression vector. Useful vectors include linear nucleic acids, plasmids, phagemids, cosmids and the like. An exemplary expression vector is pdC, in which the transcription of the immunofusin DNA is placed under the control of the enhancer and promoter of the human cytomegalovirus. See, e.g., Lo et al., 1991, Biochim. Biophys. Acta 1088:712; and Lo et al., 1998, Protein Engineering 11:495-500. An appropriate host cell can be transformed or transfected with a DNA that encodes an Sp35 polypeptide, and is used for the expression and secretion of the Sp35 polypeptide. Preferred host cells include immortal hybridoma cells, myeloma cells, 293 cells, Chinese hamster ovary (CHO) cells, Hela cells, and COS cells.

Fully intact, wild-type Fc regions display effector functions that normally are unnecessary and undesired in an Fc fusion protein according to the present invention. Therefore, certain binding sites preferably are deleted from the Fc region during the construction of the secretion cassette. For example, since coexpression with the light chain is unnecessary, the binding site for the heavy chain binding protein, Bip (Hendershot et al., 1987, Immunol. Today 8:111-114), is deleted from the CH2 domain of the Fc region of IgE, such that this site does not interfere with the efficient secretion of the immunofusin. Likewise, the cysteine residues present in the Fc regions which are responsible for binding to the light chain of the immunoglobulin should be deleted or substituted with another amino acid, such that these cysteine residues do not interfere with the proper folding of the Fc region when it is produced as an immunofusin. Transmembrane domain sequences, such as those present in IgM, should be deleted.

The IgG1 Fc region is preferred. Alternatively, the Fc region of the other subclasses of immunoglobulin gamma (gamma-2, gamma-3 and gamma-4) can be used in the secretion cassette. The IgG1 Fc region of immunoglobulin gamma-1 is preferably used in the secretion cassette includes the hinge region (at least part), the CH2 region, and the CH3 region. In some embodiments, the Fc region of immunoglobulin gamma-1 is a $CH_2$-deleted-Fc, which includes part of the hinge region and the CH3 region, but not the CH2 region. A CH2-deleted-Fc has been described by Gillies et al., 1990, Hum. Antibod. Hybridomas, 1:47. In some embodiments, the Fc regions of IgA, IgD, IgE, or IgM, are used.

Sp35-Fc fusion proteins can be constructed in several different configurations. In one configuration the C-terminus of the Sp35 moiety is fused directly to the N-terminus of the Fc moiety. In a slightly different configuration, a short polypeptide, e.g., 2-10 amino acids, is incorporated into the fusion between the N-terminus of the Sp35 moiety and the C-terminus of the Fc moiety. Such a linker provides conformational flexibility, which may improve biological activity in some circumstances. If a sufficient portion of the hinge region is retained in the Fc moiety, the Sp35-Fc fusion will dimerize, thus forming a divalent molecule. A homogeneous population of monomeric Fc fusions will yield monospecific, bivalent dimers. A mixture of two monomeric Fc fusions each having a different specificity will yield bispecific, bivalent dimers.

Any of a number of cross-linkers that contain a corresponding amino reactive group and thiol reactive group can be used to link Sp35 to serum albumin. Examples of suitable linkers include amine reactive cross-linkers that insert a thiol reactive-maleimide, e.g., SMCC, AMAS, BMPS, MBS, EMCS, SMPB, SMPH, KMUS, and GMBS. Other suitable linkers insert a thiol reactive-haloacetate group, e.g., SBAP, SIA, SLAB. Linkers that provide a protected or non-protected thiol for reaction with sulfhydryl groups to product a reducible linkage include SPDP, SMPT, SATA, and SATP. Such reagents are commercially available (e.g., Pierce Chemicals).

Conjugation does not have to involve the N-terminus of an Sp35 polypeptide or the thiol moiety on serum albumin. For example, Sp35-albumin fusions can be obtained using genetic engineering techniques, wherein the Sp35 moiety is fused to the serum albumin gene at its N-terminus, C-terminus, or both.

Sp35 polypeptides can be fused to heterologous peptides to facilitate purification or identification of the Sp35 moiety. For example, a histidine tag can be fused to an Sp35 polypeptide to facilitate purification using commercially available chromatography media.

In some embodiments of the invention, an Sp35 fusion construct is used to enhance the production of an Sp35 moiety in bacteria. In such constructs a bacterial protein normally expressed and/or secreted at a high level is employed as the N-terminal fusion partner of an Sp35 polypeptide. See, e.g., Smith et al., 1988 Gene 67:31; Hopp et al., 1988, Biotechnology 6:1204; La Vallie et al., 1993, Biotechnology 11:187.

In some embodiments of the invention, a fusion construct includes an Sp35 moiety and a second human NgR1-binding moiety, e.g., an oligodendrocyte-myelin glycoprotein (OMgp) moiety, a myelin associated glycoprotein (MAG) moiety, or Nogo66 moiety. Advantages of such constructs include increased NgR1 binding affinity.

The full-length OMgp amino acid sequence is known in the art (Genbank accession no. P23515). Specific examples of Sp35-OMgp fusions include the following:

Sp35 (aa 34-532)+IgG1 Fc+OMgp (amino acid residues 25-400); and

Sp35 (aa 34-532)+HSA+OMgp (amino acid residues 25-400).

The full-length MAG amino acid sequence is known in the art (Genbank accession no. A61084). Specific examples of Sp35-MAG fusions include the following:

Sp35 (aa 34-532)+IgG1 Fc+MAG (amino acid residues 12-500); and

Sp35 (aa 34-532)+HSA+MAG (amino acid residues 12-500).

The full-length Nogo amino acid sequence is known in the art (NogoA Genbank accession no. AY102279). Specific examples of Sp35-Nogo fusions include the following:

Sp35 (aa 34-532)+IgG1 Fc+Nogo66 (NogoA amino acid residues 1056-1122);

Sp35 (aa 34-532)+HSA+Nogo66 (NogoA amino acid residues 1056-1122);

Sp35 (aa 34-532)+IgG1 Fc+amino Nogo (NogoA amino acid residues 1-949); and

Sp35 (aa 34-532)+HSA+amino Nogo (NogoA amino acid residues 1-949).

By fusing an Sp35 moiety at the amino and carboxy termini of a suitable fusion partner, bivalent or tetravalent forms of an Sp35 polypeptide can be obtained. For example, an Sp35 moiety can be fused to the amino and carboxy termini of an Ig moiety to produce a bivalent monomeric polypeptide containing two Sp35 moieties. Upon dimerization of two of these monomers, by virtue of the Ig moiety, a tetravalent form of an Sp35 protein is obtained. Such multivalent forms can be used to achieve increased binding affinity for the target. Multivalent forms of Sp35 also can be obtained by placing Sp35 moieties in tandem to form concatamers, which can be employed alone or fused to a fusion partner such as Ig or HSA.

Conjugated Polymers (other Than Polypeptides)

Some embodiments of the invention involve an Sp35 polypeptide wherein one or more polymers are conjugated (covalently linked) to the Sp35 polypeptide. Examples of polymers suitable for such conjugation include polypeptides (discussed above), sugar polymers and polyalkylene glycol chains. Typically, but not necessarily, a polymer is conjugated to the Sp35 polypeptide for the purpose of improving one or more of the following: solubility, stability, or bioavailability.

A preferred class of polymer for conjugation to an Sp35 polypeptide is a polyalkylene glycol. Polyethylene glycol (PEG) is particularly preferred. PEG moieties, e.g., 1, 2, 3, 4 or 5 PEG polymers, can be conjugated to each Sp35 polypeptide to increase serum half life, as compared to the Sp35 polypeptide alone. PEG moieties are non-antigenic and essentially biologically inert. PEG moieties used in the practice of the invention may be branched or unbranched.

The number of PEG moieties attached to the Sp35 polypeptide and the molecular weight of the individual PEG chains can vary. In general, the higher the molecular weight of the polymer, the fewer polymer chains attached to the polypeptide. Preferably, the total polymer mass attached to the Sp35 polypeptide is from 20 kDa to 40 kDa. Thus, if one polymer chain is attached, the preferred molecular weight of the chain is 20-40 kDa. If two chains are attached, the preferred molecular weight of each chain is 10-20 kDa. If three chains are attached, the preferred molecular weight is 7-14 kDa.

The polymer, e.g., PEG, can be linked to the Sp35 polypeptide through any suitable, exposed reactive group on the polypeptide. The exposed reactive group(s) can be, for example, an N-terminal amino group or the epsilon amino group of an internal lysine residue, or both. An activated polymer can react and covalently link at any free amino group on the Sp35 polypeptide. Free carboxylic groups, suitably activated carbonyl groups, hydroxyl, guanidyl, imidazole, oxidized carbohydrate moieties and mercapto groups of the Sp35 (if available) also can be used as reactive groups for polymer attachment.

Preferably, in a conjugation reaction, from about 1.0 to about 10 moles of activated polymer per mole of polypeptide, depending on polypeptide concentration, is employed. Usually, the ratio chosen represents a balance between maximizing the reaction while minimizing side reactions (often non-specific) that can impair the desired pharmacological activity of the Sp35 moiety. Preferably, at least 50% of the biological activity (as demonstrated, e.g., in any of the assays described herein or known in the art) of the Sp35 polypeptide is retained, and most preferably nearly 100% is retained.

The polymer can be conjugated to the Sp35 polypeptide using conventional chemistry. For example, a polyalkylene glycol moiety can be coupled to a lysine epsilon amino group of the Sp35 polypeptide. Linkage to the lysine side chain can be performed with an N-hydroxylsuccinimide (NHS) active ester such as PEG succinimidyl succinate (SS-PEG) and succinimidyl propionate (SPA-PEG). Suitable polyalkylene glycol moieties include, e.g., carboxymethyl-NHS, norleucine-NHS, SC-PEG, tresylate, aldehyde, epoxide, carbonylimidazole, and PNP carbonate. These reagents are commercially available. Additional amine reactive PEG linkers can be substituted for the succinimidyl moiety. These include, e.g., isothiocyanates, nitrophenylcarbonates, epoxides, and benzotriazole carbonates. Conditions preferably are chosen to maximize the selectivity and extent or reaction. Such optimization of reaction conditions is within ordinary skill in the art.

PEGylation can be carried out by any of the PEGylation reactions known in the art. See, e.g., Focus on Growth Factors, 3: 4-10, 1992; published European patent applications EP 0 154 316 and EP 0 401 384. PEGylation may be carried out using an acylation reaction or an alkylation reaction with a reactive polyethylene glycol molecule (or an analogous reactive water-soluble polymer).

PEGylation by acylation generally involves reacting an active ester derivative of polyethylene glycol. Any reactive PEG molecule can be employed in the PEGylation. A preferred activated PEG ester is PEG esterified to N-hydroxysuccinimide (NHS). As used herein, "acylation" includes without limitation the following types of linkages between the therapeutic protein and a water soluble polymer such as PEG: amide, carbamate, urethane, and the like. See, Bioconjugate Chem. 5: 133-140, 1994. Reaction parameters should be chosen to avoid temperature, solvent, and pH conditions that would damage or inactivate the Sp35 polypeptide.

Preferably, the connecting linkage is an amide. Preferably, at least 95% of the resulting product is mono, di- or tri-PEGylated. However, some species with higher degrees of PEGylation may be formed in amounts depending on the specific reaction conditions used. Optionally, purified PEGylated species are separated from the mixture, particularly unreacted species, by conventional purification methods, including, e.g., dialysis, salting-out, ultrafiltration, ion-exchange chromatography, gel filtration chromatography, and electrophoresis.

PEGylation by alkylation generally involves reacting a terminal aldehyde derivative of PEG with Sp35 in the presence of a reducing agent. In addition, one can manipulate the reaction conditions to favor PEGylation substantially only at the N-terminal amino group of Sp35 (i.e., a mono-PEGylated protein). In either case of mono-PEGylation or poly-PEGylation, the PEG groups are preferably attached to the protein via a —CH2-NH— group. With particular reference to the —CH2-group, this type of linkage is known as an "alkyl" linkage.

Derivatization via reductive alkylation to produce a mono-PEGylated product exploits differential reactivity of different types of primary amino groups (lysine versus the N-terminal) available for derivatization. The reaction is performed at a pH that allows one to take advantage of the pKa differences between the epsilon-amino groups of the lysine residues and that of the N-terminal amino group of the protein. By such selective derivatization, attachment of a water soluble polymer that contains a reactive group such as an aldehyde, to a protein is controlled: the conjugation with the polymer takes place predominantly at the N-terminus of the protein and no significant modification of other reactive groups, such as the lysine side chain amino groups, occurs.

The polymer molecules used in both the acylation and alkylation approaches are selected from among water soluble polymers. The polymer selected should be modified to have a single reactive group, such as an active ester for acylation or an aldehyde for alkylation, preferably, so that the degree of polymerization may be controlled as provided for in the present methods. An exemplary reactive PEG aldehyde is polyethylene glycol propionaldehyde, which is water stable, or mono C1-C10 alkoxy or aryloxy derivatives thereof (see, U.S. Pat. No. 5,252,714). The polymer may be branched or unbranched. For the acylation reactions, the polymer(s) selected should have a single reactive ester group. For reductive alkylation, the polymer(s) selected should have a single reactive aldehyde group. Generally, the water soluble polymer will not be selected from naturally-occurring glycosyl residues since these are usually made more conveniently by mammalian recombinant expression systems.

Methods for preparing a PEGylated Sp35 generally includes the steps of (a) reacting a Sp35 protein or polypeptide with polyethylene glycol (such as a reactive ester or aldehyde derivative of PEG) under conditions whereby the molecule becomes attached to one or more PEG groups, and (b) obtaining the reaction product(s). In general, the optimal reaction conditions for the acylation reactions will be determined case by case based on known parameters and the desired result. For example, the larger the ratio of PEG:protein, the greater the percentage of poly-PEGylated product.

Reductive alkylation to produce a substantially homogeneous population of mono-polymer/Sp35 generally includes the steps of: (a) reacting a Sp35 protein or polypeptide with a reactive PEG molecule under reductive alkylation conditions, at a pH suitable to pen-nit selective modification of the N-terminal amino group of Sp35; and (b) obtaining the reaction product(s).

For a substantially homogeneous population of mono-polymer/Sp35, the reductive alkylation reaction conditions are those that permit the selective attachment of the water soluble polymer moiety to the N-terminus of Sp35. Such reaction conditions generally provide for pKa differences between the lysine side chain amino groups and the N-terminal amino group. For purposes of the present invention, the preferred pH is in the range of 3-9, preferably 3-6.

Sp35 polypeptides can include a tag, e.g., a moiety that can be subsequently released by proteolysis. Thus, the lysine moiety can be selectively modified by first reacting a His-tag modified with a low molecular weight linker such as Traut's reagent (Pierce) which will react with both the lysine and N-terminus, and then releasing the his tag. The polypeptide will then contain a free SH group that can be selectively modified with a PEG containing a thiol reactive head group such as a maleimide group, a vinylsulfone group, a haloacetate group, or a free or protected SH.

Traut's reagent can be replaced with any linker that will set up a specific site for PEG attachment. For example, Traut's reagent can be replaced with SPDP, SMPT, SATA, or SATP (Pierce). Similarly one could react the protein with an amine reactive linker that inserts a maleimide (for example SMCC, AMAS, BMPS, MBS, EMCS, SMPB, SMPH, KMUS, or GMBS), a haloacetate group (SBAP, SIA, SIAB), or a vinylsulfone group and react the resulting product with a PEG that contains a free SH.

In some embodiments, the polyalkylene glycol moiety is coupled to a cysteine group of the Sp35 polypeptide. Coupling can be effected using, e.g., a maleimide group, a vinylsulfone group, a haloacetate group, or a thiol group.

Optionally, the Sp35 polypeptide is conjugated to the polyethylene glycol moiety through a labile bond. The labile bond can be cleaved in, e.g., biochemical hydrolysis, proteolysis, or sulfhydryl cleavage. For example, the bond can be cleaved under in vivo (physiological) conditions.

The reactions may take place by any suitable method used for reacting biologically active materials with inert polymers, preferably at about pH 5-8, e.g., pH 5, 6, 7, or 8, if the reactive groups are on the alpha amino group at the N-terminus. Generally the process involves preparing an activated polymer and thereafter reacting the protein with the activated polymer to produce the soluble protein suitable for formulation.

Vectors

The invention provides vectors comprising the nucleic acids encoding Sp35 polypeptides. The choice of vector and expression control sequences to which the nucleic acids of this invention is operably linked depends on the functional properties desired, e.g., protein expression, and the host cell to be transformed.

Expression control elements useful for regulating the expression of an operably linked coding sequence are known in the art. Examples include, but are not limited to, inducible promoters, constitutive promoters, secretion signals, and other regulatory elements. When an inducible promoter is used, it can be controlled, e.g., by a change in nutrient status, or a change in temperature, in the host cell medium.

The vector can include a prokaryotic replicon, i.e., a DNA sequence having the ability to direct autonomous replication and maintenance of the recombinant DNA molecule extrachromosomally in a bacterial host cell. Such replicons are well known in the art. In addition, vectors that include a prokaryotic replicon may also include a gene whose expression confers a detectable marker such as a drug resistance. Examples of bacterial drug resistance genes are those that confer resistance to ampicillin or tetracycline.

Vectors that include a prokaryotic replicon can also include a prokaryotic or bacteriophage promoter for directing expression of the coding gene sequences in a bacterial host cell. Promoter sequences compatible with bacterial hosts are typically provided in plasmid vectors containing convenient restriction sites for insertion of a DNA segment to be expressed. Examples of such plasmid vectors are pUC8, pUC9, pBR322 and pBR329 (BioRad), pPL and pKK223 (Pharmacia). Any suitable prokaryotic host can be used to express a recombinant DNA molecule encoding a protein of the invention.

Eukaryotic cell expression vectors are known in the art and are commercially available. Typically, such vectors contain convenient restriction sites for insertion of the desired DNA segment. Exemplary vectors include pSVL and pKSV-10 (Pharmacia), pBPV-1, pML2d (International Biotechnologies), pTDT1 (ATCC 31255), retroviral expression vector pMIG, adenovirus shuttle vector pDC315, and AAV vectors.

Eukaryotic cell expression vectors may include a selectable marker, e.g., a drug resistance gene. The neomycin phosphotransferase (neo) gene (Southern et al., 1982, J. Mol. Anal. Genet. 1:327-341) is an example of such a gene.

To express the antibodies or antibody fragments, DNAs encoding partial or full-length light and heavy chains are inserted into expression vectors such as plasmids, retroviruses, cosmids, YACs, EBV-derived episomes, and the like. The expression vector and expression control sequences are chosen to be compatible with the expression host cell used. The antibody light chain gene and the antibody heavy chain gene can be inserted into separate vector. In some embodiments, both genes are inserted into the same expression vector.

A convenient vector is one that encodes a functionally complete human $C_H$ or $C_L$ immunoglobulin sequence. Preferably, restriction sites engineered so that any $V_H$ or $V_L$ sequence can be easily inserted and expressed. In such vectors, splicing usually occurs between the splice donor site in the inserted J region and the splice acceptor site preceding the human C region, and also at the splice regions that occur within the human $C_H$ exons. Polyadenylation and transcription termination occur at native chromosomal sites downstream of the coding regions. The recombinant expression vector can also encode a signal peptide that facilitates secretion of the antibody chain from a host cell.

Preferred regulatory sequences for mammalian host cell expression include viral elements that direct high levels of protein expression in mammalian cells, such as promoters and enhancers derived from retroviral LTRs, cytomegalovirus (CMV) (such as the CMV promoter/enhancer), Simian Virus 40 (SV40) (such as the SV40 promoter/enhancer), adenovirus, (e.g., the adenovirus major late promoter (AdMLP)), polyoma and strong mammalian promoters such as native immunoglobulin and actin promoters. For further description of viral regulatory elements, and sequences thereof, see e.g., Stinski U.S. Pat. No. 5,168,062; Bell U.S. Pat. No. 4,510,245; and Schaffner U.S. Pat. No. 4,968,615.

The recombinant expression vectors may carry sequences that regulate replication of the vector in host cells (e.g., origins of replication) and selectable marker genes. The selectable marker gene facilitates selection of host cells into which the vector has been introduced (see e.g., Axel U.S. Pat. Nos. 4,399,216; 4,634,665 and 5,179,017). For example, typically the selectable marker gene confers resistance to drugs, such as G418, hygromycin or methotrexate, on a host cell into which the vector has been introduced. Preferred selectable marker genes include the dihydrofolate reductase (DHFR) gene (for use in dhfr⁻ host cells with methotrexate selection/amplification) and the neo gene (for G418 selection).

Nucleic acid molecules encoding Sp35 polypeptides and anti-Sp35 antibodies, and vectors comprising these nucleic acid molecules, can be used for transformation of a suitable host cell. Transformation can be by any suitable method. Methods for introduction of exogenous DNA into mammalian cells are well known in the art and include dextran-mediated transfection, calcium phosphate precipitation, polybrene-mediated transfection, protoplast fusion, electroporation, encapsulation of the polynucleotide(s) in liposomes, and direct microinjection of the DNA into nuclei. In addition, nucleic acid molecules may be introduced into mammalian cells by viral vectors.

Transformation of host cells can be accomplished by conventional methods suited to the vector and host cell employed. For transformation of prokaryotic host cells, electroporation and salt treatment methods can be employed (Cohen et al., 1972, Proc. Natl. Acad. Sci. USA 69:2110-2114). For transformation of vertebrate cells, electroporation, cationic lipid or salt treatment methods can be employed. See, e.g., Graham et al., 1973, Virology 52:456-467; Wigler et al., 1979, Proc. Natl. Acad. Sci. USA 76:1373-1376f.

Mammalian cell lines available as hosts for expression are known in the art and include many immortalized cell lines available from the American Type Culture Collection (ATCC). These include, inter alia, Chinese hamster ovary (CHO) cells, NSO, SP2 cells, HeLa cells, baby hamster kidney (BHK) cells, monkey kidney cells (COS), human hepatocellular carcinoma cells (e.g., Hep G2), A549 cells, and a number of other cell lines.

Expression of polypeptides from production cell lines can be enhanced using known techniques. For example, the glutamine synthetase (GS) system is commonly used for enhancing expression under certain conditions. See, e.g., European Patent Nos. 0216846, 0256055, and 0323997 and European Patent Application No. 89303964.4.

Host Cells

Host cells can be prokaryotic or eukaryotic. Preferred eukaryotic host cells include, but are not limited to, yeast and mammalian cells, e.g., Chinese hamster ovary (CHO) cells (ATCC Accession No. CCL61), NIH Swiss mouse embryo cells NIH-3T3 (ATCC Accession No. CRL1658), and baby hamster kidney cells (BHK). Other useful eukaryotic host cells include insect cells and plant cells. Exemplary prokaryotic host cells are E. coli and Streptomyces.

Formulations

Compositions containing Sp35 polypeptides, anti-Sp35 antibodies, or antigen binding fragments of anti-Sp35 antibodies may contain suitable pharmaceutically acceptable carriers. For example, they may contain excipients and/or auxiliaries that facilitate processing of the active compounds into preparations designed for delivery to the site of action. Suitable formulations for parenteral administration include aqueous solutions of the active compounds in water-soluble form, for example, water-soluble salts. In addition, suspensions of the active compounds as appropriate oily injection suspensions may be administered. Suitable lipophilic solvents or vehicles include fatty oils, for example, sesame oil, or synthetic fatty acid esters, for example, ethyl oleate or triglycerides. Aqueous injection suspensions may contain substances that increase the viscosity of the suspension include, for example, sodium carboxymethyl cellulose, sorbitol and dextran. Optionally, the suspension may also contain stabilizers. Liposomes also can be used to encapsulate the molecules of the invention for delivery into cells or interstitial spaces. Exemplary pharmaceutically acceptable carriers are physiologically compatible solvents, dispersion media, coatings, antibacterial and antifungal agents, isotonic and absorption delaying agents, water, saline, phosphate buffered saline, dextrose, glycerol, ethanol and the like. In some embodiments, the composition comprises isotonic agents, for example, sugars, polyalcohols such as mannitol, sorbitol, or sodium chloride. In some embodiments, the compositions comprise pharmaceutically acceptable substances such as wetting or minor amounts of auxiliary substances such as wetting or emulsifying agents, preservatives or buffers, which enhance the shelf life or effectiveness of the active ingredients.

Compositions of the invention may be in a variety of forms, including, for example, liquid (e.g., injectable and infusible solutions), dispersions, suspensions, semi-solid and solid dosage forms. The preferred form depends on the mode of administration and therapeutic application.

The composition can be formulated as a solution, micro emulsion, dispersion, liposome, or other ordered structure suitable to high drug concentration. Sterile injectable solutions can be prepared by incorporating the active ingredient in the required amount in an appropriate solvent with one or a combination of ingredients enumerated above, as required, followed by filtered sterilization. Generally, dispersions are prepared by incorporating the active ingredient into a sterile vehicle that contains a basic dispersion medium and the required other ingredients from those enumerated above. In the case of sterile powders for the preparation of sterile injectable solutions, the preferred methods of preparation are vacuum drying and freeze-drying that yields a powder of the active ingredient plus any additional desired ingredient from a previously sterile-filtered solution. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition an agent that delays absorption, for example, monostearate salts and gelatin.

The active ingredient can be formulated with a controlled-release formulation or device. Examples of such formulations and devices include implants, transdermal patches, and microencapsulated delivery systems. Biodegradable, biocompatible polymers can be used, for example, ethylene vinyl acetate, polyanhydrides, polyglycolic acid, collagen, polyorthoesters, and polylactic acid. Methods for the preparation of such formulations and devices are known in the art. See e.g., Sustained and Controlled Release Drug Delivery Systems, J. R. Robinson, ed., Marcel Dekker, Inc., New York, 1978.

Injectable depot formulations can be made by forming microencapsulated matrices of the drug in biodegradable polymers such as polylactide-polyglycolide. Depending on the ratio of drug to polymer, and the nature of the polymer employed, the rate of drug release can be controlled. Other exemplary biodegradable polymers are polyorthoesters and polyanhydrides. Depot injectable formulations also can be prepared by entrapping the drug in liposomes or microemulsions.

Supplementary active compounds can be incorporated into the compositions. In some embodiments, an Sp35 polypeptide, anti-Sp35 antibody or fragment thereof is coadministered with an anti-NgR1 antibody, or an antigen-binding fragments thereof, or soluble NgR1 polypeptides or NgR1 fusion protein.

Dosage regimens may be adjusted to provide the optimum desired response. For example, a single bolus may be administered, several divided doses may be administered over time, or the dose may be proportionally reduced or increased as indicated by the exigencies of the therapeutic situation. It is advantageous to formulate parenteral compositions in dosage unit form for ease of administration and uniformity of dosage. See, e.g., Remington's Pharmaceutical Sciences (Mack Pub. Co., Easton, Pa. 1980).

In addition to the active compound, the liquid dosage form may contain inert ingredients such as water, ethyl alcohol, ethyl carbonate, ethyl acetate, benzyl alcohol, benzyl benzoate, propylene glycol, 1,3-butylene glycol, dimethylformamide, oils, glycerol, tetrahydrofurfuryl alcohol, polyethylene glycols, and fatty acid esters of sorbitan.

Gene Therapy

An Sp35 polypeptide can be produced in vivo in a mammal, e.g., a human patient, using a gene therapy approach to treatment of a CNS disease, disorder or injury in which reducing inhibition of axonal extension would be therapeutically beneficial. This involves administration of a suitable Sp35 polypeptide-encoding nucleic acid operably linked to suitable expression control sequences. Preferably, these sequences are incorporated into a viral vector. Suitable viral vectors for such gene therapy include adenoviral vectors, lentiviral vectors, baculoviral vectors, Epstein Barr viral vectors, papovaviral vectors, vaccinia viral vectors, herpes simplex viral vectors, and adeno associated virus (AAV) vectors. The viral vector can be a replication-defective viral vector. A preferred adenoviral vector has a deletion in its E1 gene or E3 gene. When an adenoviral vector is used, preferably the mammal is not exposed to a nucleic acid encoding a selectable marker gene.

EXAMPLES

The invention is further illustrated by the following experimental examples. The examples are provided for illustrative purposes only, and are not to be construed as limiting the scope or content of the invention in any way.

Example 1

Sp35 Expression Pattern

Expression of Sp35 in human tissues was evaluated by Northern blot analysis. Multiple tissue blots containing 12 human major tissues or 14 human CNS tissues were hybridized overnight at 68° C. with $P^{32}$ labeled Sp35 probe (nucleotides 150-450 of the Sp35 cDNA sequence). The blots were washed 3 times with 2×SSC, 0.5% SDS, then 3 times with 0.5×SSC, 0.1% SDS. The blot was then exposed to X-ray film and the mRNA levels visualized by autoradiography.

Sp35 was highly expressed in the human brain but not in heart, skeletal muscle, colon, thymus, spleen, kidney, liver, small intestine, placenta, lung and peripheral blood leukocytes. Sp35 was expressed in all brain tissues tested, including tissues isolated from frontal cortex, posterior cortex, entorhinal cortex, hippocampus, olfactory bulb, striatum, thalamus, cerebellum, midbrains, pons, medulla and spinal cord. A gradient of gene expression along the rostral/cordal axis was observed for Sp35, with highest levels in the cortical cortex and lowest levels in the spinal cord.

Immunohistochemical (IHC) staining was used to determine if Sp35 is expressed in specific brain cells. 4% paraformaldehyde fixed rat brains, spinal cord sections, or primary granular neuron cultures were incubated with primary antibodies to Sp35, as indicated, followed by secondary antibodies conjugated to Alexa 480 or 590 (Molecular Probes Inc.). The sections were then mounted in Vectashield and visualized by fluorescence microscopy. The anti-Sp35 specific antibodies used for IHC were generated from a Fab phage display library using MorPhosys technology.

Sp35 is expressed specifically in neurons and oligodendrocytes, but not in astrocytes. This was determined in experiments in which Rat brain tissue sections were stained with various agents, including anti-astrocyte marker GFAP, an antibody to an oligodendrocyte marker (O4), and an antibody to the neuronal marker βIII tubulin, all counterstained with an anti-Sp35 antibody. Oligodendrocytes and neurons were intensely stained with the anti-Sp35 antibody. No staining of astrocytes was observed.

As an independent confirmation of the expression pattern of Sp35, we performed semi quantitative RT-PCR using mRNA extracted (Ambion kit) from rat primary cell cultures of purified astrocytes, oligodendrocytes, and cerebellum granular neurons. Forward primer AAGGCCCAGCAGGT-GTTTGTGGA (SEQ ID NO: 14) and reverse primer TACTC-GATCTCGATGTTGTGCTTT (SEQ ID NO: 15) were used. Following 26 cycles, a strong band was observed in the mRNA from neurons, a distinct but weaker signal was detected in oligodendrocyte mRNA, and no band was observed in astrocytes.

Example 2

Sp35-Fc Fusion Protein

To study the biological function of Sp35, a construct was made fusing the extra-cellular portion of human Sp35 (residuse 1-531) to the hinge and Fc region of human IgG1. A partial coding sequence for human Sp35 was obtained by PCR from clone 227.2 (Incyte) using the forward primer 5'CAGCAGGTCGACGCGGCCGCATGCTGGCGGGGG-GCGT3' (SEQ ID NO: 16) and reverse primer 5'CAGCAG-GTCGACCTCGCCCGGCTGGTTGG3' (SEQ ID NO: 17).

The blunt end PCR product was subcloned into the SrfI site of the PCR SCRIPT AMP vector (Stratagene) to create PCR SCRIPT AMP-sp35. A SalI fragment was isolated from PCR SCRIPT AMP-sp35 and subcloned into the PCRCAMP Ig vector (derivative of Stratagene vector PCR SCRIPT AMP wherein the Fc gamma sequence is subcloned as a SalI(5') to NotI(3') fragment fusing the Sp35 signal sequence and ectodomain sequence (codons 1-531) in-frame with sequences encoding the hinge and Fc region of human Ig 1. Correct isolates were identified, and a NotI fragment encompassing the Sp35 Fc fragment was subcloned into the single Not I cloning site of the 293E expression vector, CH274, a derivative of commercial expression vector REP4 (Invitrogen). The Sp35-Fc fusion encoded by the new vector, CH274/sp35-Fc, was confirmed by DNA sequencing as plasmid GT123.

Stable cell lines expressing Sp35-Fc fusion protein were generated by electroporation of CHO host cells DG44 with plasmid GT123. Transfected CHO cells were cultured in alpha minus MEM in the presence of 10% dialyzed serum and 4 mM glutamine to select for nucleoside-independent growth. Fourteen days post-transfection, cells were fed fresh media. To screen for cells expressing Sp35-Fc, CHO cells were labeled with Phycoerythrin (PE)-labeled goat anti-human IgG (Jackson Labs) and subjected to high speed flow cytometry sorting in a FACS Mo-Flo (Cytomation). The cells that expressed the highest levels of Sp35-Ig were selected. These cells were expanded in culture for 7 days, then re-labeled and re-sorted. Cells expressing the highest levels of Sp35-Ig were isolated as individual clones in 96-well plates. These clones were grown for two weeks and then fed fresh media one day prior to FACS analysis to check for expression levels. Clones that expressed the highest levels of Sp35-Fc were expanded, and frozen cell banks were established. The cell lines were adapted to grow in suspension culture in the serum free media BCM16. The titer of Sp35-Fc produced by these clones was determined by growing cell lines at 37° C. for 4-5 passages, then growing the cells to 50% maximal cell density and culturing them for 10-15 days at 28° C. until the viable cell density dropped to 75%. At this time, the culture media were harvested, cleared of cells and debris by centrifugation, and the culture supernatants titered for Sp35-Fc levels by Western blot analysis using an anti-human Ig antibody (Jackson Lab) as the probe.

Sp35-Fc fusion protein was purified from the clarified culture medium as follows: 9 ml of 1M HEPES pH 7.5 was added to 900 ml of conditioned medium. The medium was batch loaded for 3 hr at 4° C. onto 3 ml of Protein A Sepharose (Pharmacia). The resin was collected in a 1.5 cm (I.D.) column, and washed four times with 3 ml PBS, two times with 4 ml of PBS containing 800 mM NaCl, and then again with 3 mL of PBS. The Sp35-Fc was eluted from the column with 25 mM $NaH_2PO_4$ pH 2.8, 100 mM NaCl in 1.5 mL fractions and neutralized by adding 75 µL of 0.5 M $NaH_2PO_4$ pH 8.6. Peak protein-containing fractions were identified by absorbence at 280 nm, pooled, and subjected to further purification on a 1 mL Protein A column. Prior to loading, NaCl was added to 600 mM and HEPES pH 7.5 to 50 mM. The column was washed twice with 600 µL of 10 mM HEPES pH 7.5, 1 M NaCl, and then with 1 mL PBS. Sp35-Fc was eluted from the column with 25 mM $NaH_2PO_4$ pH 2.8, 100 mM NaCl, collecting 0.5 mL fractions, and neutralized by adding 25 µL of 0.5 M $NaH_2PO_4$ pH 8.6. Peak protein-containing fractions were identified by absorbence at 280 nm and pooled. By reducing SDS-PAGE, the Sp35-Ig migrated as a single band (>95% pure) with an apparent mass of 90 kDa. Under non-reducing conditions, the protein ran as a dimer with an approximate mass of 180 kDa. The purified Sp35-Fc was aliquoted and stored at −70° C. The NotI fragment of GT123, which contains Sp35 amino acids 1-531 and human IgG1 Fc, was subcloned into the PV90 vector NotI site to create DB002.

Example 3

His-AP-Sp35 Fusion Protein

To study and isolate the receptor for Sp35, the protein was expressed in COS7 and CHO cells as a His-tagged-alkaline phosphatase (His-AP) fusion protein. The plasmid was constructed as follows: The extracellular domain of Sp35 (a.a. 34-532) was PCR amplified using primers (forward) 5'-AAT-TAAGAATTCACGGGCTGCCCGCCCCGCTGCGAGT-3' (SEQ ID NO: 18), containing an Eco RI cleavage site (underlined), and (reverse) 5'-TATATTTCTAGATCACTCGCCC GGCTGGTTGGAGATGAAAGCGA-3' (SEQ ID NO: 19), containing an Xba I cleavage site (underlined). The PCR product was cleaved with Xba I, the resulting sticky-end filled in with T4 DNA polymerase, then digested with Eco RI and gel purified. The digested product was ligated into a Hind III-filled in/EcoR I His-AP fragment from the His-AP-pcDNA 1.1 vector (Invitrogen). The His-AP Sp35 fragment was digested with Hind III and Eco RI, filled in, then ligated into the Not I-filled site in vector pV90. The DNA sequence of the insert was confirmed by DNA sequencing.

COS7 cells were split the day before transfection. His-AP-Sp35 vector DNA (8 µg) was used to transfect $5 \times 10^6$ cells using lipofectamine (Invitrogen). The conditioned medium was harvested 48 hr post transfection.

We developed a CHO cell line expressing the His-AP-Sp35 fusion protein using the pV90 plasmid. CHO host cells DG44 ($2 \times 10^6$ cells) were transfected with 100 µg of plasmid by electroporation. Cells were cultured in alpha minus MEM in the presence of 10% dialyzed serum and 4 mM glutamine to select for nucleoside-independent growth. Fourteen days post transfection cells were fed fresh media in anticipation of screening by FACS Mo-Flo (Cytomation) sorting. Transfected CHO cells were labeled with the mouse monoclonal antibody 8B6 directed against human placental alkaline phosphatase (Sigma). A secondary antibody, PE-labeled goat anti-mouse IgG, was used to produce a signal specific for transfected cells. After PE-labeling, cells were subjected to high speed flow cytometry sorting and the top 5% selected.

To produce conditioned medium with His-AP-Sp35, the cells that expressed the highest levels of HIS-ApSp35 were selected. The cell lines were adapted to grow in suspension culture in serum free media (BCM16). The titer of His-AP-Sp35 that was produced by these clones was determined by growing cell lines at 37° C. for 4-5 passages, then growing the cells to 50% of maximal cell density and culturing them for 10-15 days at 28° C. until the viable cell density dropped to 75%. The culture media were harvested, cleared of cells and debris by centrifugation, and the culture supernatants titered for His-AP-Sp35 levels by western blot analysis using anti-human AP antibody (Jackson Labs) as the probe.

His-AP-Sp35 was purified from the conditioned medium as follows: 400 mL of conditioned medium from CHO cells expressing His-AP-Sp35 was diluted with 400 mL of water. Triethanolamine pH 8.5 was added to 25 mM from a 0.5 M stock and the sample was batch loaded for 2 hours at 4° C. onto 6 ml of Fractogel TMAE (EM Industries) anion exchange resin. The resin was collected in a 1.5 cm (I.D.) column, and washed two times with 6 mL of 10 mM HEPES pH7.5, 50 mM NaCl. The AP-Sp35 was eluted from the column with 10 mM HEPES pH 7.5, 200 mM NaCl in 2 mL fractions. Peak fractions were identified by monitoring AP activity and by SDS-PAGE. The flow-through fraction from the TMAE column was further diluted with 300 ml of water and loaded in batch overnight at 4° C. onto 6 ml of TMAE resin. The resin was collected and washed as described above and eluted with 10 mM HEPES pH 7.5, 150 mM NaCl. Peak fractions again were identified by monitoring AP activity and by SDS-PAGE. His-AP-Sp35 from the first column was 50% pure and AP-Sp35 from the second column was 90% pure. Under reducing conditions, the His-AP-Sp35 migrated on SDS-PAGE gels with an apparent mass of 130 kDa. While the 90% pure material was appropriate for most investigations, for some studies the His-AP-Sp35 was further purified on Ni-NTA agarose resin (Qiagen). NaCl was added to the elution fractions from the TMAE column to 800 mM and 0.5 M triethanolamine pH. 8.5 and 1M imidazole pH 7.0 was added to 25 mM and 15 mM, respectively. 4.5 ml of the sample was loaded onto a 400 µL NiNTA column. The column was washed three times with 25 mM Triethanolamine pH 8.5, 800 mM NaCl, 15 mM imidazole, and the His-AP-Sp35 was eluted from the column with 200 mM imidazole pH 7.0, 350 mM NaCl, collecting 200 µL fractions. Peak AP-containing fractions were pooled and dialyzed overnight against 250 volumes of 10 mM HEPES pH 7.5, 200 mM NaCl. $MgCl_2$ and $ZnCl_2$ were added to the retentive to 2 and 0.25 mM, respectively. The final product was greater than 95% pure by SDS-PAGE, and ran as a single band with mass of approximately 140 kDa under reducing conditions.

The Sp35 constructs were also engineered as Fc fusions. An Sp-35 LRR-Fc construct was generated by PCR using primers (forward) 5'CTTGACACG GGATCCGCGGCCG-CATGCTGGCGGGGGGCGTGAGG3' (SEQ ID NO: 20) and (reverse) 5'GCAGCGGGGCGGGCAGCCCGTGGC-CGAGCCTGACAGCACTGAGCC3' (SEQ ID NO: 21). The PCR product was inserted into the NotI site of PV90 vector. Sp35 IG-Fc construct was generated by PCR using primers (forward) 5'CTTGACACGGGATCCGCGGCCGCAT-GCTGGCGGGGGGC GTGAGG3' (SEQ ID NO: 22) and (reverse) 5'GTCCCGGATGCGGGCGCGGG CCGAGCCT-GACAGCACTGAGCCCAG3' (SEQ ID NO: 23). The PCR product was inserted into the NotI site of PV90 vector. The proteins were expressed in CHO cells and purified using a protein A sepharose column.

Example 4

Sp35 Binding to NgR1-Expressing Cells

Four different methods were used to show Sp35 binding to NgR1. First we detected the interaction in a direct binding assay in which the alkaline phosphatase-Sp35 conjugate (AP-Sp35) was incubated with NgR1 expressing cells and binding assessed using a chromogenic AP detection reagent. 90% confluent COS7 cells were grown on 100 mm tissue culture dishes and transfected with NgR1 expressing plasmids using Fugene 6 reagents (Roche). After 48 hours, the transfected cells were washed once with HBH (Hank's balanced salt buffer, 1 mg/ml BSA, 20 mM HEPES, pH 7.0), and then incubated for 1.5 hr at 23° C. with 4 µg/ml of the AP-Sp35 fusion protein in HBH. The cells were washed with ice-cold HBH buffer 3 times for 3 min each, then fixed with 3.7% formaldehyde in 20 mM HEPES, pH 7.0, 150 mM NaCl for 15 min, and transferred back into HBH buffer. Endogenous heat-labile AP was heat-inactivated for 2 hours at 67° C. Bound AP-Sp35 was detected by incubation with nitro blue tetrazolium NBT (Roche). Ap-Sp35 bound to COS7 cells expressing human NgR1 receptor, but not to control COS7 cells transfected with the vector alone. A punctate staining pattern for NgR1 was observed, reflecting that only a fraction, probably 50% of the cells, were transfected with the NgR1.

To better quantify binding, we performed the same experiment but parallel cell samples were treated with 8, 4, 2, 1, 0.5, 0.125, 0.06 µg/ml of the AP-Sp35. Bound AP was incubated with 4-nitrophenyl phosphate and AP activity assessed in a 96-well plate reader (Molecular Devices). From these data, we estimated that the EC50 for binding of Ap-Sp35 to human NgR1 was approximately 6 nM.

Second, we detected binding of Sp35 to NgR1 in an ELISA approach. ELISA plates (Costar) were coated with 10 µg/ml soluble NgR1-Fc receptors (sNgR310-Fc containing rat NgR1 peptide 35-310 fused to the hinge and Fc of rat IgG1 and sNgR344-Fc containing rat NgR1 peptide 35-344 fused to the rat IgG1) in 0.1M $NaHCO_3$, pH 9.0 for 1 hr at 37° C. The plates were blocked and washed with 25 mM Hepes, pH 7.0, 0.1% BSA, 0.1% ovalbumin, 0.1% non-fat dried milk and 0.001% $NaN_3$. AP-Sp35 protein, 4 µg/ml, was added to the plate and incubated overnight at 4° C. The plates were then washed with 10 mM Tris pH 7.5, 150 mM NaCl and bound AP detected using 10 µg/ml of the chromogenic substrate 4-nitrophenyl phosphate diluted in 0.1 M glycine, 1 mM $MgCl_2$, 1 mM $ZnCl_2$ pH 10.5. The $OD_{410}$ was determined in an ELISA reader (Molecular Devices) equipped with the Softmax program. AP-Sp35 bound to immobilized sNgR-344-Fc but not the sNgR-3,0-Fc protein, indicating that the longer version of NgR1 was required for Sp35 binding. We were able to compete the binding of AP-Sp35 to sNgR344-Fc NgR1 by 80% by pre-incubating the AP Sp35 with 100-fold excess of sNgR344-Fc. No competition of binding was seen using a hedgehog-rat Ig 1 fusion protein as a rat Ig fusion control protein.

Third, we detected the binding of Sp35 to NgR1 by co-immunoprecipitating Sp35 with NgR1. For this study, 80% confluent COS7 cells, grown on 100 mm tissue culture dishes, were transfected with plasmids encoding Sp35-hemagglutinin (Sp35-HA) and NgR-FLAG using Fugene 6 reagents (Roche) 48 hours after transfection, cells were harvested and lysed in 1 ml lysis buffer (50 mM HEPES, pH 7.5, 150 mM NaCl, 1.5 mM $MgCl_2$, 1 mM EGTA, 1% Triton X-100 and 10% glycerol) at 4° C. for 30 min. The lysate was then centrifuged at 14,000×g for 15 min, and the supernatants collected and incubated 4° C. overnight with agitation, using anti-HA affinity matrix (Roche). The samples were washed 3 times with 1 ml of lysis buffer, then boiled for 3 minutes in Laemmli sample buffer, subjected to 4-15% SDS-PAGE, and analyzed by immuno-blotting with Anti-FLAG M2 antibody (Sigma). The anti-HA tag affinity resin collected a complex containing both Sp35-HA and FLAG-NgR, as is evident by the presence of FLAG. This complex was not seen in lysates from control transfections in which cells were treated with Sp35-HA plasmid or FLAG-NgR1 plasmid alone, or cells that were co-transfected with the Flag-NgR1 and a HA-tagged control protein that does not bind NgR1.

Sp35-HA was made as follows. The Sp35 signal sequence and extracellular domain (amino acids 1-531) was PCR amplified using primers 5'ATATTCTAGAATGCTGG-CGGGGGGCGTGAG3' (SEQ ID NO: 24) and 5'ATAT ACTAGTGTCGTTGCCGCCCGCGTTGG3' (SEQ ID NO: 25) containing XbaI and SpeI sites (underlined). The PCR product was digested by XbaI and SpeI and inserted into the vector pCGCHA between the Xba I and Spe I sites. The sequence of the insert was confirmed by DNA sequencing. The FLAG NgR1 construct was gift from Dr. Zhigang He (Nature, Vol 420, Nov. 7, 2002).

Fourth, we showed that Ap-Sp35 bound to rat cerebellum granular neurons (CGN) which express NgR1. For this experiment, 90% confluent postnatal day 8 CGN cells were grown on 100 mm tissue culture dishes. After 48 hours, the cells were washed once with HBH buffer, and then incubated with 4 µg/ml of AP-Sp35 in HBH buffer for 1.5 hour at 23° C.

The cells were then washed with ice-cold HBH 3 times for 3 minutes each, then fixed with 3.7% formaldehyde in 20 mM HEPES, pH 7.0, and 150 mM NaCl for 15 min, and transferred back to HBH. Endogenous heat labile AP was heat-inactivated for 2 hours at 67° C. Bound AP-Sp35 was detected by incubation with nitro blue tetrazolium NBT (Roche). AP-Sp35 bound to postnatal day 8 cerebellum granular neurons, which express NgR1. The binding of AP-Sp35 to the neurons was inhibited by treating the CGN with PIPLC (5 units/ml) which cleaves most GPI anchored proteins from membrane surfaces. Since NgR1 is a GPI-linked protein, this result further supports the notion that Sp35 is binding to NgR1 on CGN cells.

Example 5

Co-localization of Sp35 with NgR1

To determine whether Sp35 and NgR1 are expressed in the same neurons, we performed a co-localization study. 4% paraformaldehyde-fixed rat p8 primary granular neuron cultures were incubated with antibodies against Sp35 and NgR1 (Santa Cruz), and then with the appropriate Alexa-labeled secondary antibodies (Molecular Probes Inc.). The cells were visualized by con-focal fluorescence microscopy. Neurons were intensely stained by the Sp35 and NgR1 antibodies. Both proteins were expressed in the cell bodies and axons of neurons. To aid in the co-localization analysis, different colored probes were used for the 2 types of antibodies. When the stains (red for NgR positive cells and green for Sp35 positive cells) were merged we saw a yellow color throughout the cell indicating that the two proteins were co-localized within the neurons.

Example 6

NgR1 Binding Sites within Sp35

We used deletion mapping to define the specific domains of Sp35 involved in NgR1 interactions. The following deletion constructs were made using the Stratagene Quikchange Mutagenesis kit. We verified all vector constructs by DNA sequencing of the modified inserts.

His-AP-Sp35b which contains the leucine rich repeat domain of Sp35 plus the basic region (a.a 34-432) was cloned from the His-AP-Sp35 (a.a. 34-532) vector by PCR. Primers used were 5'CCCAGCAGGTGTTTGTGGACGAGTG-ATCTAGGGCCGCGGATCCCTG-3' (SEQ ID NO: 26) and 5'-CAGGGATCCGCGGCCCTAGATCACTCGTCCACA-AACACCTGCTGGG-3' (SEQ ID NO: 27).

His-AP-Sp35d, which encodes the Ig domain of Sp35 plus the basic region (a.a 417-531), was cloned from the His-AP-Sp35a (a.a. 37-531) vector by PCR. Primers used were 5'CGCCGCGCACCCGGGTGAATTCCGCGCCCGCATC-CGGGACCGC-3' (SEQ ID NO: 28) and 5'-GCGGTCCCG-GATGCGGGCGC GGAATTCACCCGGGTGCGCGGCG-3' (SEQ ID NO: 29).

His-AP-Sp35e, which encodes only the Ig domain (a.a 425-531), was cloned from the His-AP-Sp35(aa 34-532) vector by PCR. Primers used were 5'-CGCCGCGCAC-CCGGGTGAATTCGCCCAGCAGGTGTTTGTGGAC-3' (SEQ ID NO: 30) and 5'-GTCCACAAACACCT-GCTGGGCGAATTCACCCGGGTGCGCGGCG-3' (SEQ ID NO: 31).

A commercial mutagenesis kit and protocol (Stratagene Quikchange) were used to mutate amino acid 456 (from arginine to glutamic acid) and amino acid 458 (from histidine to valine) of Sp35 in the vector His-AP-Sp35 (34-532). The primers used were 5'-CATCCTCTGGCTCTCAC-CCGAAAAGGTACTGGTCTCAGCCAAGAGC-3' (SEQ ID NO: 32) and 5'-GCTCTTGGCTGAGACCAGTAC-CTTTTCGGGTGAGAGCCAGAGGATG-3' (SEQ ID NO: 33).

His-AP-Sp35 deletion constructs (FIG. 3) were engineered in pV90 expression vectors and expressed in 293 cells. The conditioned medium was collected and the AP adducts purified by sequential chromatography steps on Fractogel TMAE resin and NiNTA agarose. The purified proteins were tested for binding to NgR1 expressed on COS7 cells. The three constructs all bound weakly to Sp35. These results indicated that the Sp35 LRR repeat 1-14 (amino acid 34 to 417) and the Ig domain of Sp35 (amino acid 425-531) both contribute to Sp35 binding to NgR1. The Ig domain showed higher affinity than the LRR domain.

A structural model for the Ig domain of Sp35 was generated using the NCAM crystal structure as a framework (Rasmussen et al., 2000, Nat. Struct. Biol. 7:389-393). From this model, we observed a loop (residue numbers 454-458, amino acids: SPRKH; SEQ ID NO: 34) that might be involved in binding. To test this hypothesis, we engineered an Sp35 construct in which residues R at 456 and H at 458 were changed into E and V, respectively. When this construct was tested for NgR1 binding, we observed a >10 fold drop in signal. As an alternative approach to test the contribution of this loop region in binding, we synthesized a peptide corresponding to the sequence LSPRKH (SEQ ID NO: 10) that we cyclized by adding cysteines at the N and C terminus of the peptide. Upon binding to NgR1, this peptide blocks, inhibits, or interferes with the function of NgR1.

Example 7

Sp35 Induces p8 CGN Fasciculation

To determine the biological function of Sp35 in neurons, we incubated Sp35-Fc with postnatal day 8 granular neurons to see if Sp35 can regulate neurite out-growth. Labtek culture slides (8 well) were coated with 0.1 mg/ml poly-D-lysine (Sigma) before spotting of Sp35-Fc protein (16 µg/well protein). The slides were dried overnight, then rinsed and coated with 10 µg/ml laminin (Gibco). Cerebellum granular neurons from postnatal day 8 were dissociated and seeded onto the precoated slides. The slide cultures were incubated at 37° C. in 5% $CO_2$ for 24 hours. The slides were then fixed in 4% paraformaldehyde containing 20% sucrose and stained with anti βIII tubulin (Covance TUJ1). After 24 hours, the CGN showed clear fasciculation morphology as evident by bundling of the neurons. The fasciculation was not seen in the untreated cells or Fc protein-coated sample controls.

Example 8

Effects of Sp35 on RhoA Activation/Inactivation

Sp35-Fc induced postnatal cerebellum granular neurons to undergo fasciculation. Because the signaling molecule RhoA is known to be involved in fasciculation, we determined if Sp35-Fc can regulate RhoA functions in neurons. We performed the RhoA activation experiment as follows: 293 cells or COS7 cells were transfected with expression vectors containing combinations of RhoA, Sp35 or NgR1 using Fugene 6 reagents (Roche). 48 hr post-transfection, cells were serum starved overnight, then lysed in 50 mM Tris, pH 7.5, 1% Triton X-100, 0.5% sodium deoxycholate, 0.1% SDS, 500 mM NaCl, 10 mM MgCl$_2$, plus a protease inhibitor cocktail. Cell lysates were clarified by centrifugation at 13,000×g at 4° C. for 5 minutes, and 95% of the supernatants were incubated with 20 µg of an immobilized GST-Rho binding domain affinity matrix (Rhotekin beads, Upstate Biotechnology) at 4° C. for 45 minutes. The beads were washed 3 times with wash buffer (50 mM Tris, pH 7.5, 1% Triton X-100, 150 mM NaCl, 10 mM MgCl$_2$, with protease inhibitors). GTP-bound Rho was eluted from the beads by heating at 95° C. for 5 min in SDS-PAGE sample buffer. Bound and total Rho proteins were detected by western blotting using a monoclonal antibody against RhoA (Santa Cruz). COS7 and HEK293 cells transfected with Sp35 induced RhoA activation, as evident by an increase in the amount of RhoA-GTP detected in the blot following transfection with the Sp35 gene. A further enhancement in RhoA-GTP was observed following treatment with Sp35-Fc. In contrast to the increase in RhoA-GTP following transfection with Sp35 alone, when cells were transfected with Sp35 and NgR1, RhoA was partially inactivated. Treatment of these cells with Sp35-Fc resulted in further inactivation of RhoA.

We confirmed a signaling response by Sp35 using a FLIPR assay (Molecular Devices) to determine the affects of Sp35 treatment on Ca$^{++}$ flux. We observed a significant Ca$^{++}$ flux in cells expressing Sp35 with treatment of Sp35-Fc, but not in the control cells treated with Sp35-Fc. The Ca$^{++}$ flux was reduced when cells that had been co-transfected with NgR1 and Sp35 were treated with Sp35 Fc fusion protein.

Example 9

Sp35 Protein Interaction with Itself

Because LRR domains frequently are involved in homotypic interactions, and we observed that the addition of soluble Sp35 to Sp35-transfected cells caused an increase in RhoA-GTP over what was observed with Sp35 transfections alone, we tested for Sp35 binding to itself. To perform this test, we used co-immunoprecipitation. COST cells 80% confluent, grown on 100 mm tissue culture dishes, were transfected with plasmids Sp35 HA or Sp35-FLAG, or both, using Fugene 6 reagents (Roche). Forty-eight hours after transfection, cells were harvested and lysed in 1 ml lysis buffer (50 mM HEPES, pH 7.5, 150 mM NaCl, 1.5 mM MgCl$_2$, 1 mM EGTA, 1% Triton X-100 and 10% glycerol) at 4° C. for 30 min. The lysate was then centrifuged at 14,000×g for 15 min, and the supernatants collected and incubated, at 4° C. overnight with agitation, with an anti-HA affinity matrix (Roche). The samples were then washed 3 times with 1 ml of lysis buffer, boiled in Laemmli sample buffer, subjected to 4-15% SDS-PAGE, and analyzed by immuno-blotting with anti-FLAG antibodies. The Anti-HA antibody resin captured a complex that contained Sp35-FLAG, as determined by Western blotting. This indicated a direct interaction of Sp35 with itself. We also treated cells transfected with HA-Sp35 with Sp35-Fc and used a similar immunoprecipitation approach to show that HA-Sp35 bound to Sp35-Fc.

Sp35-FLAG was made as follows. Sp35 gene extracellular domain (a. a. 1-531) was PCR amplified using primers 5'AATTAAGCGGCCGCATGCTGGCGGGGGCGT3' (SEQ ID NO: 35) and 5'AATTAAGCGGCCGCTTT-GTCATGT'3 (SEQ ID NO: 36) containing NotI sites (underlined). The PCR product was digested by NotI and inserted into the NotI site of vector pV90. The DNA sequence of the insert was confirmed by DNA sequencing.

Example 10

In Vivo Transplantation of Sp35-Transformed Cells

To determine the biological function of Sp35 in spinal cord injured rats, we infected cortical primary cultured cells (mixed cultures) with retrovirus expressing full length Sp35 or a retrovirus control, for delivery into the injured epicenter of rat spinal cords. 2×10$^6$ cells were introduced, and the rats were sacrificed at day 10. The spinal cords were fixed in 4% paraformaldehyde overnight, then dehydrated in 70%, followed by 95% ETOH. Tissue samples were imbedded in paraffin. Sections (10 microns thick) were used for immunohistochemical staining. Rats that received Sp35-expressing cells, in comparison to control, show less axon retraction and more –βIII tubulin staining near the epicenter. Increased neuronal survival in the injured rats receiving Sp35 was observed.

The Sp35 retrovirus construct was made as follows: The Sp35 gene was PCR amplified using primers 5'-GATTA-CTCGAGATGCTGGCGGGGGGCGT GAGG-3' (SEQ ID NO: 37), containing an XhoI site (underlined), and 5'CGCG-GGAATTCTCATATCATCTTCATGTTGAACTTG-3' (SEQ ID NO: 38), containing an EcoRI site (underlined). The PCR product was digested with XhoI and EcoRI, then ligated into the Retrovirus vector pMIG (which contains IRES-GFP), which was previously cleaved with XhoI and EcoRI. The new vector was named pMMC078. All isolates of pMMC078 contained inadvertent point mutations, so two isolates of pMMC078 were ligated together. pMMC078.6 was cut with XhoI and AccI and pMMC078.7 was cut with XhoI and AccI. These two fragments were ligated together to make the final correct plasmid, pMMC089. The DNA sequence of the insert was confirmed by DNA sequencing. Sp35 retrovirus was made as described. 293G cells were split the day before transfection. 8 µg Sp35-retrovirus DNA was used to transfect 5×10$^6$ cells by lipofectamine (Invitrogen). The condition medium was harvested after 92 hours post-transfection. The conditioned medium was centrifuged at 5000 g for 10 minutes, and the supernatant used as a Sp35 retrovirus stock. This stock was stored at 4° C. for 1 week or –80° C. for 6 months.

Example 11

Animal Model of Spinal Cord Injury

All surgical procedures are performed using aseptic technique. For 1 week prior to any surgical manipulation animals are handled. Ampicillin 100 mg/kg SC is administered prophylactically prior to and after surgery to reduce the incidence of bladder infection injury.

Animals are anesthetized using Midazolam at 2.5 mg/kg IP in conjunction with Isoflurane 2-3% in O$_2$ to deep anesthesia as measured by toe pinch. Animals are maintained on a circulating water heating pad for the duration of surgery and recovery. Ocular lubricant are used to prevent corneal drying and Atropine 0.05 mg/kg SC are given to reduce excess salivation. A small incision is made in the skin and the muscle retracted to expose the vertebrae. A dorsal laminectomy at the spinal level L6 (and L7 if placement of an intrathecal catheter is necessary, see below) is performed, L6/L7 and the adjacent spinous processes rigidly fixed in a spinal frame (David Kopf Instruments). A dorsal hemisection is performed at L6 with fine iridectomy scissors completely interrupting the main dorsomedial and the minor dorsolateral coticospinal tract (CST) components. Following surgery, the laminectomy site is covered with a protective material such as Durafilm, and the overlying muscle sutured with 4.0 chromic gut to protect the exposed spinal column. The skin is sutured and wiped with betadine solution.

Functional recovery of animals IS evaluated using the Basso Beattie and Bresnehan (BBB) scoring method commonly used to evaluate rats after spinal cord injury. This method quantifies the hind limb function of rats by detailed analysis of joint movement and weight bearing ability. Rats are evaluated the day after spinal cord injury then weekly thereafter.\

Immediately after CST transection, adenovirus expressing Sp35 or GFP or control virus ($10^{10}$ particles) are injected at the site of transection and regions immediately caudal and rostral to the injury site. A total of 10 µl of Adv are injected at 5 different sites (4 ul/site). For the intrathecal administration of Sp35 protein, a small hole is made into the dura of the spinal cord at 2 mm caudal to the lesion L7 and an intrathecal catheter is inserted into the subarachnoid space at L7. The catheter is slowly and gently slid above the spinal cord about 1 mm caudal to the lesion. The portion of the catheter lying outside the intrathecal space is firmly sutured in place to the surrounding tissue. A primed mini-osmotic pump (Alza corp.) containing the test material (Sp35 protein or control protein) is connected to the exposed end of the guide cannula and inserted into the subcutaneous space. Following surgery, the laminectomy sites are covered with a protective material such as Durafilm and the overlying muscle sutured with 4.0 chromic gut to protect the exposed spinal column. The skin is sutured and wiped with betadine solution.

Histological Analysis: Tract tracing surgery occurs at the time of the surgery to induce spinal cord injury. The skin on the head is shaved and wiped with Betadine and 70% alcohol. The animal is placed in a stereotaxic frame. The scalp is incised longitudinally and the periosteum is scraped from the calvaria. A hole is drilled in the skull approximately 1-2 mm in diameter, and a glass microliter needle is inserted vertically into 8 locations in the motor cortex (coordinates are determined according to the rat brain atlas of Paxinos and Waston, 1997). Approximately 50 of tract tracer material (e.g., Biotin dextran amine, 10,000M.Wt) is injected and the needle is left in place for an additional five minutes to allow diffusion of the solution. After needle removal, the hole in the scull cap is plugged with gel foam and the scalp stapled closed over the injury site. Animals are allowed to recover and receive postoperative care (described below). Four to ten weeks later the animals are deeply anesthetized (Inactin 100-110 mg/kg ip) and perfused for histology as described below. The tract tracer is carried by anterograde transport mechanisms down the cortical spinal tract towards the caudal end of the spinal cord and provides a means to quantify anatomical connectivity within the corticospinal tract.

For immunohistochemistry experiments, animals are deeply anesthetized with Inactin (100-110 mg/kg IP) 2-8 weeks after surgery to induce injury. The chest cavity is opened and the heart is exposed, to allow for perfusion. A cannula is inserted into the left ventricle through which 100 cc ice-cold PBS is pushed slowly (a hole will be cut in the right ventricle to allow fluid escape). This is followed by a slow but steady drip of 4% paraformaldehyde (50-100 ml) until fixation of eyes/ears/toes is obvious. Spinal cords are removed, with care to minimize alteration of the injury site, frozen in OCT, sectioned, and processed for immunohistochemistry. Other tissues optionally are also collected for later analysis. The animals receiving adenovirus Sp35 showed increased axon sprouting as determined by βIII tubulin staining for neuron axon.

Example 12

Sp-35 Viral Vector Constructs

A pMIG-derived Sp-35 viral vector was made as follows. The full-length Sp35 coding sequence was PCR amplified using primers 5'-GATTACTCGAGATGCTGGCGGGG-GGCGTGAGG-3' (SEQ ID NO: 37), containing an XhoI site, and 5' CGCGGGAATTCTCATATCATCTTCATGTTG-AACTTG-3' (SEQ ID NO: 38), containing an EcoRI site. The PCR product was cut with XhoI and EcoRI, then ligated into the Retrovirus vector pMIG (Cheng et al, 1996, Nat. Biotechnol. 145:576) which was cut with XhoI and EcoRI. This vector was designated pMMC078. All isolates of pMMC078 contained point mutations, so two isolates of pMMC078 were ligated together. Vector pMMC078.6 was cut with XhoI and AccI and pMMC078.7 was cut with XhoI and AccI. These two fragments were ligated to make the plasmid, pMMC089.

A pMIG-derived Sp35-HA viral vector was made as follows. A fragment encoding Sp35 amino acids 326-614 in frame with the HA sequence was obtained by using PCR with primers 5'-GCCTTCCGCGGCCTCAACTACCTGCGCG-TGCTC-3' (SEQ ID NO: 39), containing a SacII site, and 5'-CCGGAATTCTCAAGCGTAATCAGGAACGTCGTA-AGGG*TATATCA*TCTTCATGTTGAACTTGCGGGGCG-CGTCGGC-3' (SEQ ID NO: 40), with pMMC089 serving as a template. The longer primer includes the HA coding sequence (italics) after Sp35 codon 614 and before the EcoR I site. The PCR product was then cut with Sac II and EcoR I, and used to replace the Sac II-EcoR I fragment containing wild-type Sp35 codons 326-614 in the pMIG-derived retroviral vector.

An Sp35-baculovirus HA vector was made as follows. The Sp35-HA coding sequence from Sp35-HA retroviral vector was cut out with Xho I and EcoR I, blunt-ended, and cloned into Bg12-fill in site of baculo viral shuttle vector pBV-CZPG (U.S. Pat. Nos. 6,190,887; and 6,338,953), replacing LacZ gene under CMV promoter.

An Sp35-adenoviral vector was made as follows. Sp35-IRES-GFP coding sequence from the Sp35-retroviral was cut out with Xho I-fill in and Nhe I, then cloned into the EcoR1-fill in/Nhe I sites of the Adenovirus shuttle vector pDC315, under minimal CMV promoter.

Example 13

Animal Model of Remyelination

Female Long Evans rats are used in all studies. Rats are anaesthetized using Isoflurane and the T3/4 exposed and a dorsal hemi-laminectomy performed. The chemical demyelinating agent, lysolecithin (3 µl of 1% lysolecithin in 0.9% saline), is then injected into the right side of dorsal columns of the spinal cord 0.5-1 mm below the surface of the cord). Appropriate analgesic treatment is administered before and after surgery.

Three days later, the injection site is re-exposed (under isoflurane anesthesia, with appropriate analgesic treatment) and the following therapies injected into the injured spinal cord and an adenovirus vector encoding protein Sp35/control protein is injected into the injury site. $10^{10}$ particles of adenovirus encoding Sp35 or GFP control in a volume of 10 µl will be injected into injured rat spinal cord in up to 5 different sites in and around the site of lysolecithin-induced demyelination. A volume of not greater than 2 µl is injected at each of the 5 injection sites. For histological analysis of spinal cord demyelination/remyelination 2, 3, 4 or 6 weeks after surgery, animals are deeply anesthetized with inactin (100-110 mg/kg ip) and perfused with fixative via the heart. The spinal cord is then removed and processed for analysis. The animal receiving Sp35 treatment showed increased axon myelination as determined by IHC using anti-MBP protein antibody or luxol fast blue.

Example 14

Sp35 RNAi

To address the role of Sp35 in brain function, we introduced the lentivirus Sp35 RNAi into postnatal 8 CGN cells. Sp35 RNAi infected cells had shorter neurites and higher rates of proliferation than control cells. These results indicate a role for Sp35 in regulating RhoA activation.

Murine and rat Sp35 DNA sequences were compared to find homologous regions to use for candidate shRNAs. $CH_{324}$ was constructed by annealing oligonucleotides LV1-035 and LV1-036 and ligating to HpaI and XhoI digested pLL3.7. The oligonucleotides were purchased from MWG. The sequences are:

```
LV1-035 (sense oligo)
                                (SEQ ID NO: 41)
5'TGATCGTCATCCTGCTAGACTTCAAGAGAGTCTAGCAGGATGACGATC
TTTTTTC LV1-036 (antisense oligo)
                                (SEQ ID NO: 42)
5'TCGAGAAAAAAGATCGTCATCCTGCTAGACTCTCTTGAAGTCTAGCAG
GATGACGATCA.
```

Prior to producing virus, DNA from pLL3.7 or candidate shRNA in pLL3.7 were cotransfected with murine SP35-HA tagged plasmid at a ratio of 5 to 1 into CHO cells in 6 well format. Knockdown was analysed by western blot detection of SP35-HA tag from transfected CHO cell lysates as well as by northern blot of total RNA prepared from duplicate wells. The blot was probed with a 0.7 kb fragment of mSP35. Assays were performed 48 hours post-transfection (data not shown). Viruses were produced from the best candidate for use in rat neuronal cultures. The vector, additional methodology and virus production were as described in Rubinson et al. "A lentivirus-based system to functionally silence genes in primary mammalian cells, stem cells and transgenic mice by RNA interference." Nat. Genet. 33, 401-6 (2003).

Example 15

RhoA Activation

COS7 cells co-expressing NgR1 and SP35 showed no changes in RhoA/GTP levels in response to OMgp. This suggested that the SP35/NgR1 complex is not sufficient for mediating signal transduction by a myelin inhibitor.

Figure 4:
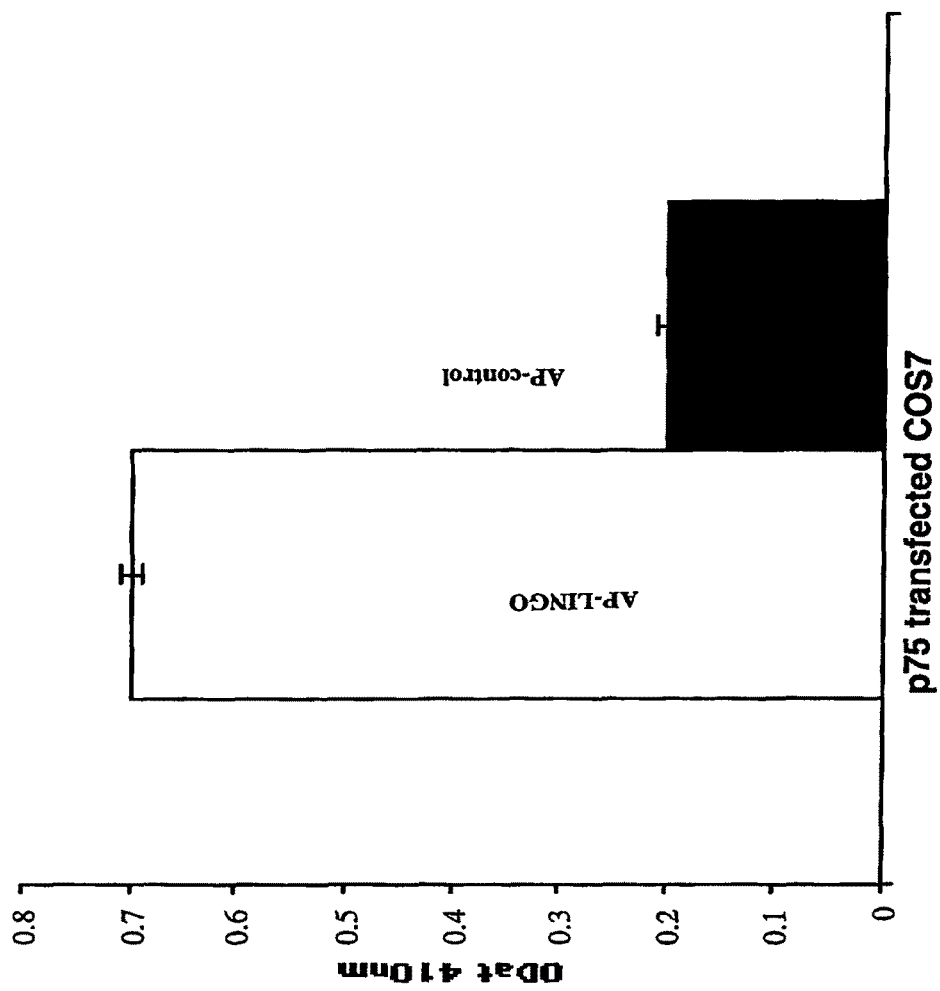
FIG. 4 is a histogram summarizing data on SP35 binding to COS7 cells transfected with an expression vector encoding rat p75 or a vector control. After 48 hours, AP-SP35 or AP was incubated with the cells. Bound AP was detected using chromogenic AP detection reagent.

We explored the possibility that a ternary complex of SP35/NgR1/p75 mediates signaling. Two approaches were used to evaluate interactions between SP35, NgR1 and p75. First, binding was evaluated in a direct binding assay using an AP-SP35 conjugate. The AP-SP35 conjugate bound weakly to p75-expressing cells. AP-P75 bound to NgR1 expressing cells. The binding of AP-SP35 to NgR1 and p75 were measured by ELISA (FIG. 4). Second, binding of SP35 to NgR1 and p75 was evaluated by a co-immunoprecipitation from COS7 cells co-expressing SP35 NgR1 and p75. An anti-NgR1 antibody immunoprecipated a complex containing SP35 and p75. An anti SP35 antibody also immunoprecipitated a complex containing p75. The interaction and co-immunopreicipitation data provided evidence for a direct interaction between SP35, NgR1 and p75. We used confocal microscopy and antibodies against SP35, p75 and NgR1 to show that SP35, NgR1 and p75 co-localize to cell bodies and axons of p7 CG neurons from rat.

Figure 5:
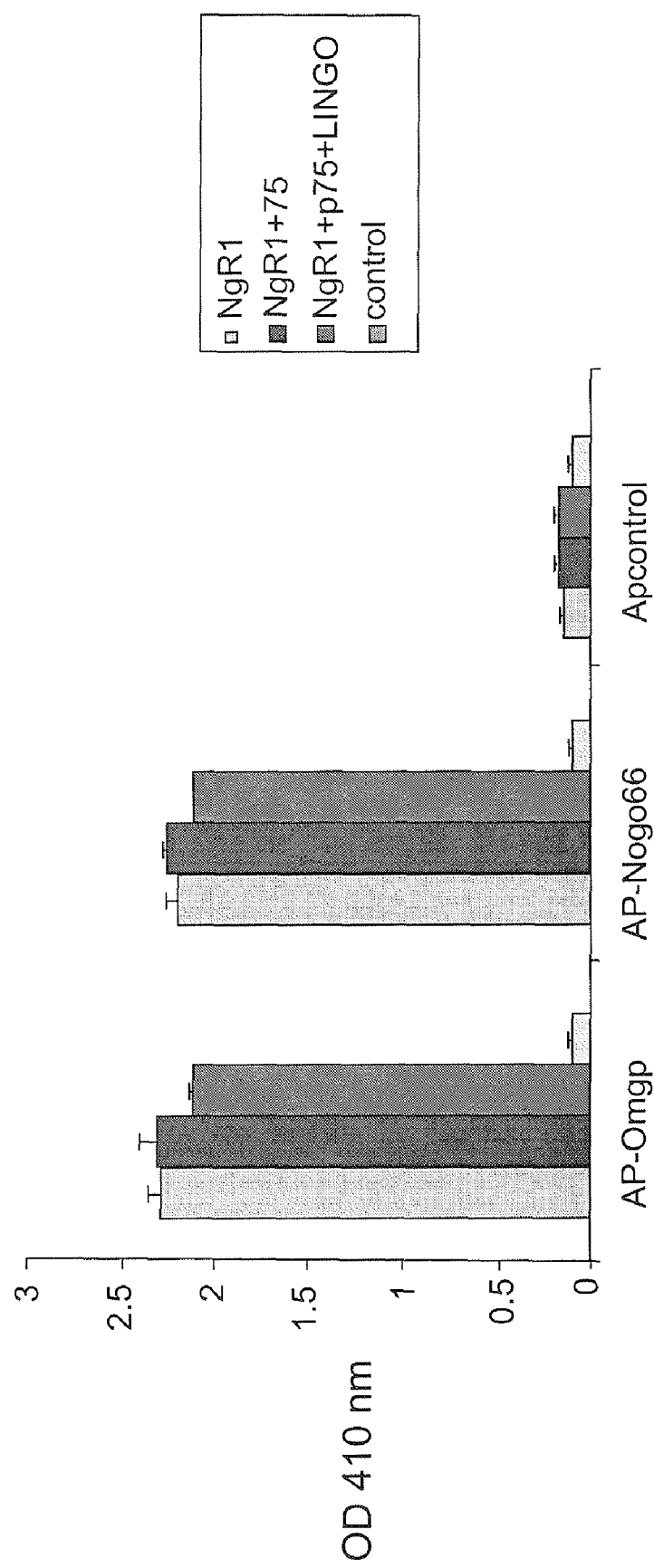
FIG. 5 is a histogram summarizing data on binding of AP-Omgp, and AP-Nogo-66 to COS7 cells transfected with an expression vector encoding NgR1; NgR1 and p75; NgR1, p75, and SP35, or a vector control. After 48 hours, AP-Omgp, AP-Nogo-66 or AP was incubated with the cells. Bound AP was detected using chromogenic AP detection reagent.

Next we showed that the combination of SP35, NgR1 and p75 is sufficient for the activities of the myelin inhibitor. Non-neuronal COS7 cells were engineered to express all three components. Using these cells, we showed that RhoA/GTP levels were up-regulated by OMgp. OMgp-Fc treatment increased RhoA/GTP levels in SP35/p75/NgR1 co-expressing cells, as compared to other combinations of these three components. We confirmed expression of the proteins by Western blotting of COS7 cells lysates. The affinity of myelin inhibitors binding to NgR1 were not affected by the presence of p75 or p75 and SP35. The combined results support a model whereby a ternary complex of NgR1, SP35 and p75 is required for RhoA regulation in the presence of NgR1 ligands (FIG. 5).

Figure 6:
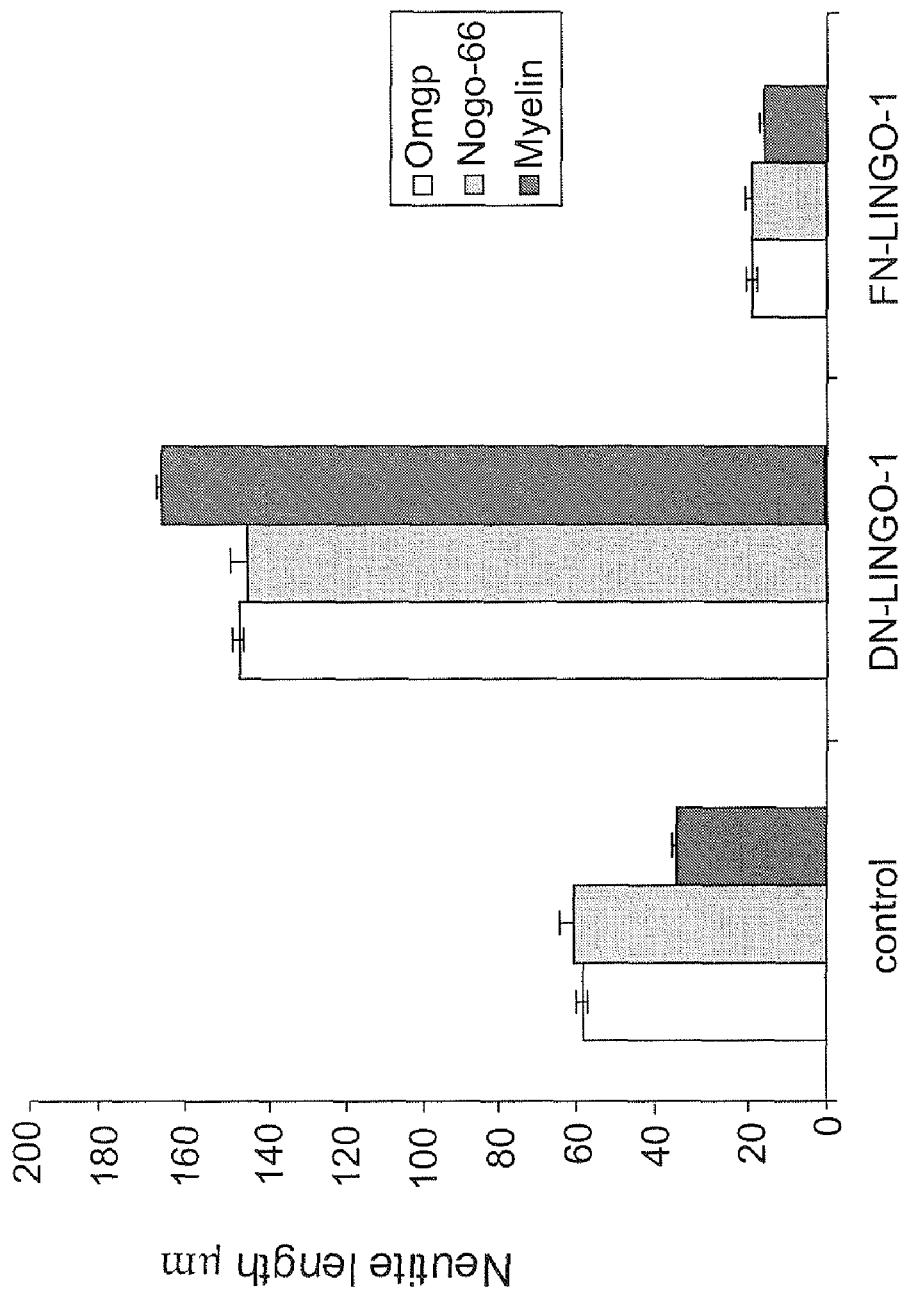
FIG. 6 is a histogram summarizing data on the relief of inhibitory activity of myelin inhibitors on neurite outgrowth in vitro. Neurite length was measured on postnatal day 7 rat cerebellar granular neurons expressing DN-Sp35, full-length Sp35, or controls cultured on immobolized substrate Omgp, Myelin and Nogo-66. DN-SP35 transfected cells exhibited diminished response to inhibitory substrates. Neurite length was quantified from 1000 neurons per treatment group from two independent experiments ($p<0.01$).
Figure 7:
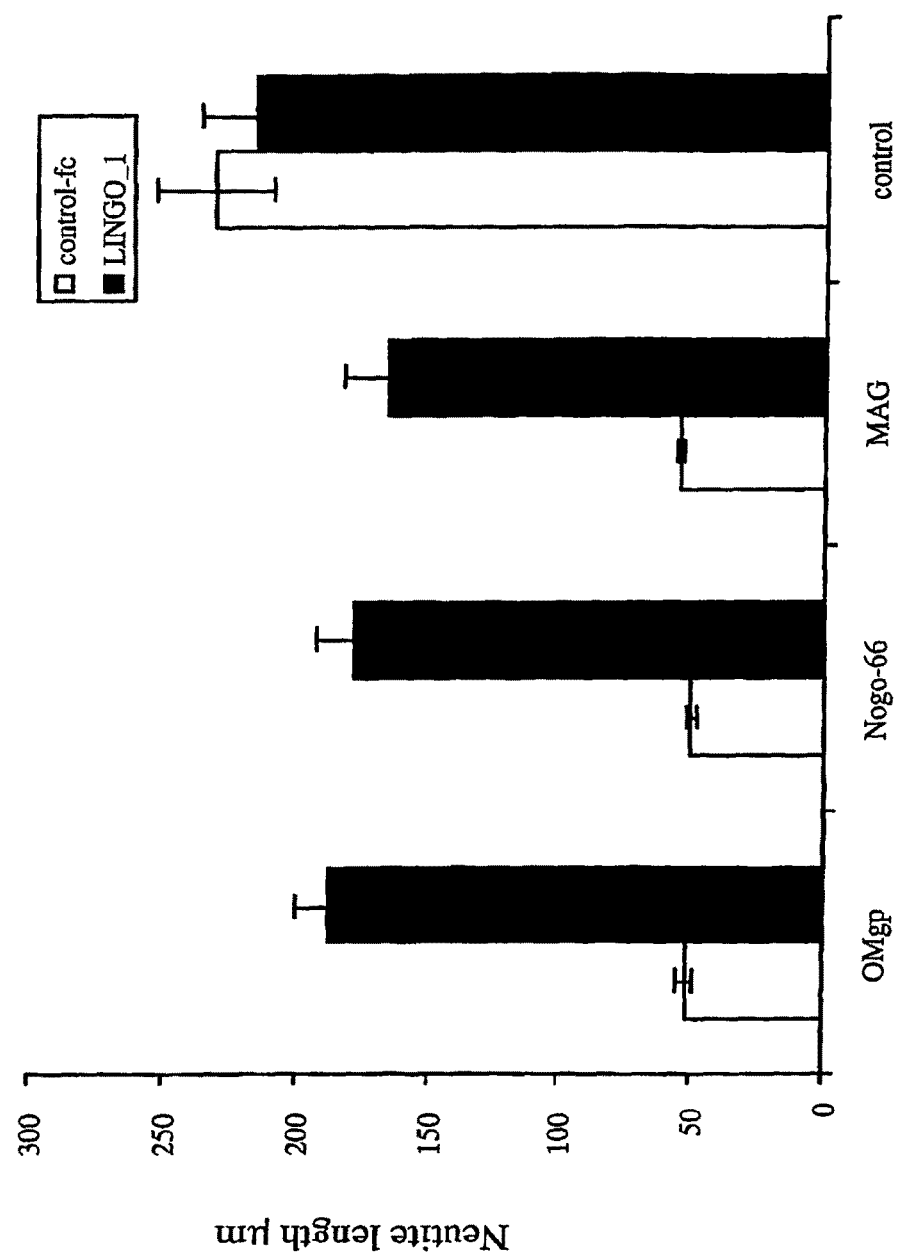
FIG. 7 is a histogram summarizing data on reversal of inhibitory activity of myelin inhibitors by SP35-Fc. Neurite length of postnatal day 7 rat cerebellar granular neurons (1000 neurons) cultured on immobilized substrate OMgp, Myelin or Nogo-66 in the presence or absence of SP35-Fc. SP35-Fc reduced the neurite outgrowth inhibition caused by Omgp, Nogo-66 and MAG. Neurite length was quantified from 1000 neurons per treatment group from two independent experiments ($p<0.01$).

SP35 contains a cytoplasmic domain that has potential direct or indirect involvement in signaling. To determine the role of the cytoplasmic domain, we produced a cytoplasmic domain truncation of SP35 (amino acids 34 to 576 of SEQ ID NO: 2), to function in a dominant negative manner by forming an unproductive, ternary complex incapable of signaling. We designated this molecule with the cytoplasmic domain truncation "DN-SP35" (for dominant negative SP35). We transfected postnatal day 7(p7) CG neurons with full-length SP35 or DN-SP35, and then assayed for response to the inhibitory myelin components (Omgp, myelin and Nogo66). As shown in FIG. 6, DN-SP35 transfected cells failed to respond to the inhibitory myelin components and showed longer neurites than controls. In contrast, cells transfected with the full length SP35 construct showed enhanced response to the inhibitory substrates, and had shorter neurites as compared to controls. This demonstrated that DN-SP35 acts as a competitor to attenuate neurite outgrowth inhibition caused by myelin components. We expected that exogenous, soluble SP35-Fc also would bind NgR1 and block the action of inhibitory substrates. As shown in FIG. 7, SP35-Fc reduced the neurite outgrowth inhibition by Omgp, Nogo66 and MAG.

Example 16

Neuroprotective Activity

Equal numbers of rat p6 cerebellar granule neurons was plated in each well of a 12-well cell culture plate in the presence or absence of 50 nM of sp35-Fc protein. These poly-D-lysine plates have been pre-coated [dried down] with 10 μg of CNS myelin, or 200 ng of Nogo66, MAG and OMgp or control-Fc. The neuronal cultures were maintained for 1-7 days at 37° C. and 5% $CO_2$. The neurons were healthy and grew well in the PBS control wells independent of sp35-Fc treatment with full neurite extension [determined by neuronal specific marker, III tubulin] as examined after 3 days. In the absence of sp35-Fc, the neurons did not grow well in the wells coated with myelin, Nogo66, MAG and OMgp. There was minimum neurite sprouting [short and distorted] and the neurons did not appear to be healthy, with rounded cell body and condensed nuclear materials. DAPI staining demonstrated that the number of neurons detected in these wells was less than that in the PBS control wells, suggesting neuronal loss. In the presence of sp35-Fc, long neurites were present and the neurons appeared healthy. DAPI staining demonstrated a higher neuronal number in these wells than those that did not receive the sp35-Fc. The data are summarized in Table 2 below.

TABLE 2

| In the absence of sp35-Fc | | |
|---|---|---|
| Dried down substrate: | OMgp/Nogo/MAG/ myelin | Fc control |
| neurite extension | short distorted | long extended |
| cell body morphology | rounded | spread |
| nuclear materials | condensed | clear |
| neuron number at the end of expt | reduced | same as control Fc |
| In the presence of sp35-Fc | | |
| Dried down substrate: | OMgp/Nogo/MAG/ myelin | Fc control |
| neurite extension | long extended | long extended |
| cell body morphology | spread | spread |
| nuclear materials | clear | clear |
| neuron number at the end of expt | less reduced that control FC | same as control Fc |

These data indicated that a soluble form of Sp35, e.g., Sp35-Fc, possesses neuroprotective activity.

In spinal cord hemi-transected (T9, SCT) rats, β-III tubulin staining of the spinal cord sections showed a substantial loss of neurons at the lesion site. A recombinant virus expressing sp35 was used to infect the SCT animals at the lesion site. Histological staining of these spinal cords showed an increased number of neurons around the lesion site compared to the control group that was infected with the vector virus. This is consistent with the in vitro experimental findings described above, and further indicates neuroprotective properties associated with Sp35.

Example 17

Sp35 in Animal Model of Spinal Cord Injury

Figure 9:
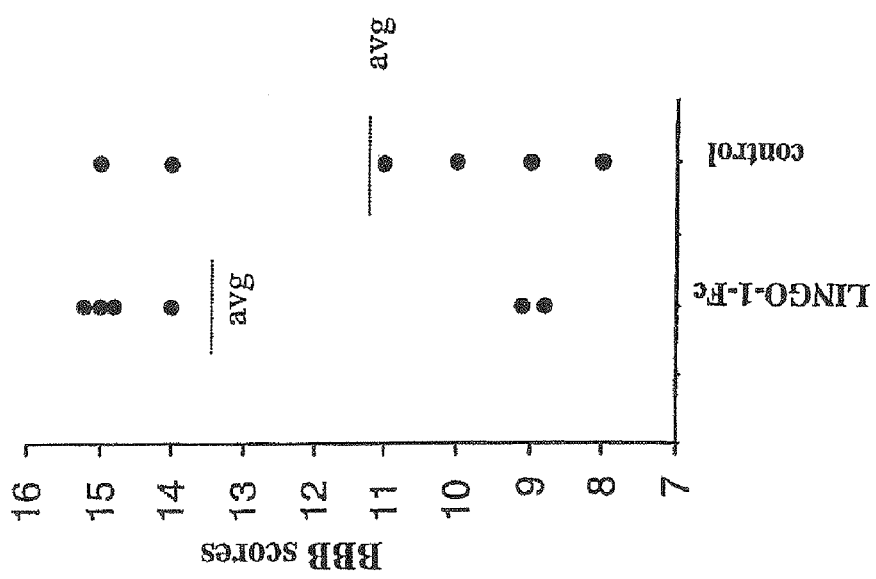
FIG. 9 is a graph showing individual animal BBB scores at week four in the experiment summarized in FIG. 8.
Figure 8:
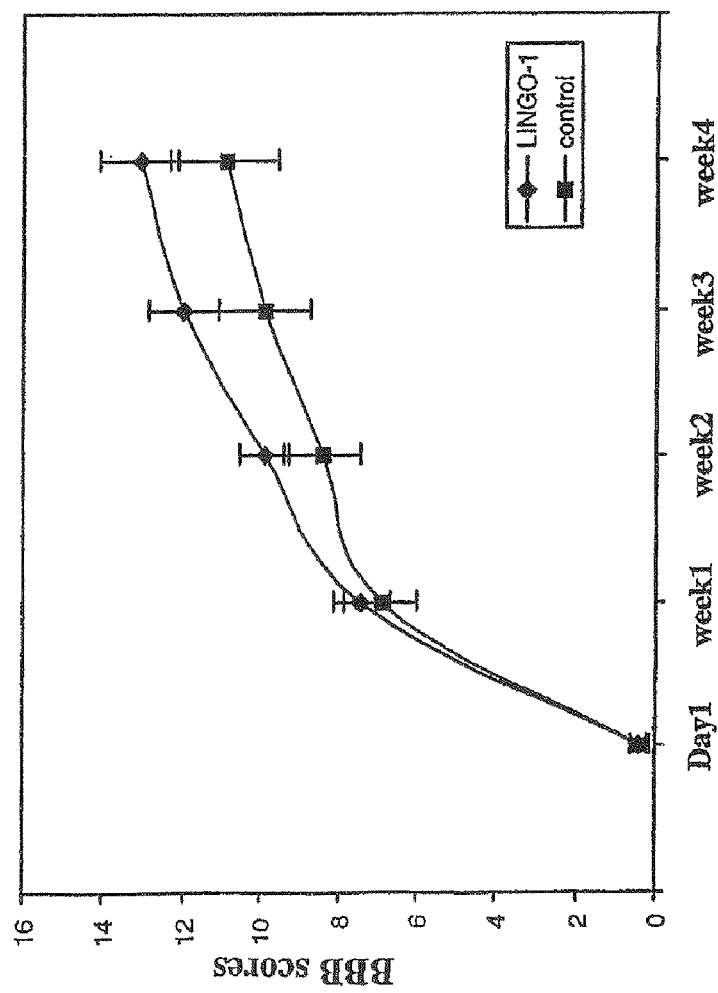
FIG. 8 is a graph summarizing data from an experiment showing that intrathecal-administered Sp35-Fc improves functional recovery after dorsal hemisection in a rat. The locomoter BBB score measured as a function of time after dorsal hemisection in control (IgG) or Sp35-Fc-treated rats (8 animals per group). Treatment was initiated at the time of spinal cord injury.

Since Sp35-Fc reduced neurite outgrowth inhibition caused by OMgp, Nogo-66 and MAG in vitro, we expected the molecule to promote functional recovery of CNS injuries in vivo. To confirm this, we administered Sp35-Fc to spinal chord hemisected rats, i.e., an animal model of acute CNS trauma. As shown in FIG. 8 and FIG. 9, Sp35-Fc treated rats demonstrated significantly improved functional recovery, compared to control rats treated with IgG.

Spinal cord injury and behavioral analysis were performed as follows. All surgical procedures were performed in accordance with the guidelines of the Biogen Institutional Animal Use and Care Committee. Female Long Evans rats (190-210 g, Charles River, Wilmington, Mass.) were anesthetized using 2.5 mg/kg Midazolam, I.P. and 2-3% Fluothane in $O_2$. A dorsal laminectomy was performed at spinal level T6 and T7. A dorsal hemisection was performed, completely interrupting the main dorsomedial and the minor dorsolateral corticospinal tract (CST) components. Immediately after CST transection an intrathecal catheter was inserted into the subarachnoid space at T7 and connected to a primed mini-osmotic pump (Alzet model 2004) inserted into the subcutaneous space. Mini-osmotic pumps delivered Hu IgG isotype control protein (5 mg/ml, n=5, Pharmingen), PBS (n=3) soluble Hu Sp35-Ig fusion protein (4.3 mg/ml, n=8) at a rate of 0.25 µl/h. Following surgery, the laminectomy site was sutured and the skin wound stapled closed. Postoperative care included analgesia (Buprenorphine 0.05 mg/kg s.c.) for 3 days and antibiotic treatment (Ampicillin 100 mg/kg s.c.twice daily) for 7 days after surgery. Bladders were expressed manually twice a day for the duration of the study (28 days) or until return of function (the time of which was noted). All animals were blindly scored using the open-field BBB scoring system (Basso et al., 1995, *J. Neurotrauma* 12:1-21; Ono et al., 2003, *J. Neurosci.* 23:5887-5896). Rats were evaluated the day after CST transection (day 2) and weekly thereafter for 4 weeks using the Basso-Beattie-Bresnahan (BBB) locomotor rating scale. Investigators were blinded to the treatment groups for the duration of the study.

Example 18

Neuronal Survival and Axon Regeneration in the Rubro-Spinal Tract (RST) Hemi-Section Injury Model We also investigated the effects of Sp35 treatment on the regeneration of neurons in the rubro-spinal tract which directly contribute to locomotion.

Adult 9-week-old Sprague-Dawley rats (200-250 g) were anesthetized with an intraperitoneal injection of ketamine (80 mg/kg) and xylazine (8 mg/kg). Under an operating microscope, a dorsal laminectomy was performed and the seventh thoracic spinal vertebra (C7) identified. After opening the dura mater, a right hemi-section was performed at spinal cord level C7 using a pair of spring scissors. Following spinal cord hemi-section, animals received a piece of gelfoam soaked with either 100 of a 2 µg/ml solution of Sp35-Fc, or 10 µl of a 2 µg/ml solution of human Ig, or 10 µl PBS, placed on top of the lesion site. After the operations, animals in each group were subdivided for axonal tracing and behavioral analysis. The animals for axonal tracing (n=5 for each group) and behavioral analysis (n=7 for each group) were allowed to survive for 1 month.

Fluoro-Gold (FG, 6% w/v, Fluorochrome) was used to label the RST neurons that had regenerated their axons across the injury scar and reentered the caudal spinal cord. Two days prior to the end of the post-injury survival period (1 month), animals were anesthetized with an intraperitoneal injection of ketamine (80 mg/kg) and xylazine (8 mg/kg). A dorsal laminectomy was carried out and the T2 spinal segment was identified. FG at a volume of 0.5 ml was manually injected into the right T2 spinal cord using a Hamilton syringe. Two days later, the animals were anesthetized and sacrificed with a lethal dose of ketamine (150 mg/kg) and xylazine (8 mg/kg) and they were perfused intracardinally with normal saline, followed by 400 ml of fixative containing 4% paraformaldehyde in 0.1×PBS. The brains and spinal cords were removed, postfixed with paraformaldehyde overnight, and then placed in 30% phosphate-buffered sucrose. Brain and spinal cord tissue were cut into 30 mm sections on a cryostat and mounted onto gelatin-coated slides. The number of FG-labeled RST neurons on the lesion side was expressed as a percentage of the total number of FG-labeled neurons on the contra-lateral intact side. This percentage among groups was compared statistically using one-way ANOVA followed by a Tukey-Kramer multiple comparisons test. As shown in Table 3, Sp35-Fc at 2 µg/ml promoted the survival of rubro-spinal tract (RST) neurons.

TABLE 3

| Treatment | Percent Survival of RST Neurons (±S.E.M.) |
|---|---|
| PBS | 17.1 ± 2 |
| Sp35-Fc | 31.9 ± 1.5 |
| Control-Fc | 14.5 ± 2.1 |

For behavioral analysis, the use of forelimbs during spontaneous vertical exploration was examined 1 month after different treatments as described (Liu et al., 1999) with minor modifications. Rats were placed in a clear Plexiglas cylinder (15 cm in diameter and 30 cm high) that encourages use of the forelimbs for vertical exploration for 5 min. The following behaviors were scored: (1) independent use of the left (unimpaired) or right (impaired) forelimbs for contacting the wall of the cylinder; and (2) simultaneous use of both forelimbs to contact the wall of the cylinder. The vertical exploration behavior was expressed in terms of (1) percentage use of left (unimpaired) forelimb relative to the total number of impaired, unimpaired, and both limb use; (2) percentage use of right (impaired) forelimb relative to the total number of impaired, unimpaired, and both limb use; and (3) percentage use of both forelimbs relative to the total number of impaired, unimpaired, and both limb use. The differences between groups were tested by one-way ANOVA followed by Bonferroni post hoc analysis. Sp35-Fc treated animals showed significantly improved front limb movement: 30% usage for both forelimbs in Sp35-1-Fc treated animals versus 10% usage for both forelimbs in control-Fc or PBS-treated animals; 55% left (unimpaired) limb usage versus 80% usage in control-Fc or PBS-treated animals; and 29% right (impaired) limb usage versus approximately 15% in control-Fc or PBS treated animals.

Example 19

Sp35-Fc Promotes Retinal Ganglion Cell (RGC) Survival in the Optic Nerve Transection Model We further confirmed the activity of Sp35 using the optic nerve transection model, which investigates factors that affect neuronal function. Young adult female Sprague Dawley (SD) rats were used in this study. The right optic nerve of each animal was transected intraorbitally 1.5 mm from the optic disc. A piece of gelfoam soaked with 6% Fluoro-Gold (FG) was applied to the newly transected site right behind the optic disc to label the surviving retinal ganglion cells (RGCs). The animals were divided into 6 groups (n=6 in each group) receiving either Sp35-Fc, human IgG1, or just PBS, by intravitreal injection. The volume of each intravitreal injection was 4 ml while the dosage of each injection was 2 mg. The intravitreal injections were performed immediately after the optic nerve transection.

All animals were allowed to survive for 1 week. Two days before sacrificing the animals, the left optic nerve of each animal was transected and 6% FG were used to label the surviving RGCs to serve as the internal control. Animals were sacrificed with an overdose of Nembutal and the retinas dissected in 4% paraformaldehyde. Four radial cuts were made to divide the retinas into four quadrants (superior, inferior, nasal and temporal). The retinas were then post-fixed in the same fixative for 1 hour before they were flat-mounted with the mounting medium (Dako). The slides were examined under a fluorescence microscope using an ultra-violet filter (excitation wavelength=330-380 nm). Labeled RGCs were counted along the median line of each quadrants starting from the optic disc to the peripheral border of the retina at 500 mm intervals, under an eyepiece grid of 200×200 mm. The percentage of surviving RGCs resulting from each treatment was expressed by comparing the number of surviving RGCs in the injured eyes with their contra-lateral eyes. All data were expressed as mean±SEM. Statistical significance was evaluated by one way ANOVA, followed by a Tukey-Kramer post hoc test. Differences were considered significant for $p<0.05$. Sp35-Fc treated animals showed significant neuronal survival (83%) when compared to control-Fc or PBS treated animals, which each only showed approximately 50% neuronal survival.

Other Embodiments

Other embodiments are within the following claims.

The invention claimed is:

1. A method of treating a CNS disease, disorder or injury associated with neurodegeneration in a mammal in need thereof comprising administering to said mammal a therapeutically effective amount of an Sp35 antagonist.

2. The method of claim 1, wherein the Sp35 antagonist is a soluble fragment of SEQ ID NO:2.

3. The method of claim 2, wherein the soluble fragment of SEQ ID NO:2 is selected from the group consisting of:
 (a) a polypeptide comprising amino acids 34-532 of SEQ ID NO:2;
 (b) a polypeptide comprising amino acids 34-417 of SEQ ID NO:2;
 (c) a polypeptide comprising amino acids 34-432 of SEQ ID NO:2;
 (d) a polypeptide comprising amino acids 417-531 of SEQ ID NO:2;
 (e) a polypeptide comprising amino acids 425-531 of SEQ ID NO:2;
 (f) a polypeptide comprising amino acids 1-531 of SEQ ID NO:2;
 (g) a polypeptide comprising amino acids 433-493 of SEQ ID NO:2;
 (h) a polypeptide comprising an Sp35 LRR domain, an Sp35 basic region C-terminal to the LRR domain, and an Sp35 immunoglobulin (Ig) domain C-terminal to the basic region, but lacks a transmembrane domain;
 (i) a polypeptide comprising an Sp35 Ig domain, but lacking an Sp35 LRR domain, an Sp35 basic region, a transmembrane domain, and a cytoplasmic domain;
 (j) a polypeptide comprising an Sp35 LRR domain, but lacking an Sp35 Ig domain, an Sp35 basic region, a transmembrane domain, and a cytoplasmic domain;
 (k) a polypeptide as in (h), further lacking a cytoplasmic domain; and (l) a polypeptide consisting of the amino acids of SEQ ID NO:10 (LSPRKH).

4. The method of claim 2, wherein the soluble fragment of SEQ ID NO:2 is conjugated to a polymer.

5. The method of claim 4, wherein the polymer is selected from the group consisting of polyalkylene glycol, a sugar polymer, and a heterologous polypeptide.

6. The method of claim 5, wherein the heterologous polypeptide is selected from the group consisting of: an Ig polypeptide, a serum albumin polypeptide, a targeting polypeptide, a reporter polypeptide, a human NgR1-binding polypeptide, one or more cysteine residues and a purification-facilitating polypeptide.

7. The method of claim 6, wherein the Ig polypeptide is an Fc polypeptide.

8. The method of claim 1, wherein the Sp35 antagonist is an Sp35 antibody.

9. The method of claim 8, wherein said CNS disease, disorder or injury is multiple sclerosis.

10. The method of claim 1, wherein said CNS disease, disorder, or injury is selected from the group consisting of multiple sclerosis, ALS, Huntington's disease, Alzheimer's disease, Parkinson's disease, diabetic neuropathy, stroke, traumatic brain injury, optic nerve injury and spinal cord injury.

11. The method of claim 1, wherein the Sp35 antagonist is administered locally.

12. A method of treating spinal cord injury in a mammal in need thereof comprising administering to said mammal a therapeutically effective amount of an Sp35 antagonist.

13. A method of treating optic nerve injury in a mammal in need thereof comprising administering to said mammal a therapeutically effective amount of an Sp35 antagonist.

14. A method of treating multiple sclerosis in a mammal in need thereof comprising administering to said mammal a therapeutically effective amount of an Sp35 antagonist.

15. A method of treating CNS disease, disorder or injury associated with neurodegeneration in a mammal in need thereof comprising administering to said mammal a therapeutically effective amount of an interfering RNA molecule, wherein said interfering RNA molecule inhibits the expression of Sp35.

16. The method of claim 15, wherein the interfering RNA molecule comprises a nucleic acid sequence selected from the group consisting of SEQ ID NO: 41 and SEQ ID NO: 42.

* * * * *

UNITED STATES PATENT AND TRADEMARK OFFICE
Certificate

Patent No. 8,153,580 B2                                                                Patented: April 10, 2012

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Sha Mi, Belmont, MA (US); John McCoy, Reading, MA (US); R. Blake Pepinsky, Arlington, MA (US); Daniel H. S. Lee, Sudbury, MA (US); and Alexey A. Lugovskoy, Cambridge, MA (US).

Signed and Sealed this Sixteenth Day of October 2012.

MANJUNATH RAO
*Supervisory Patent Examiner*
Art Unit 1656
Technology Center 1600

SEQUENCE LISTING

```
<160> NUMBER OF SEQ ID NOS: 41

<210> SEQ ID NO 1
<211> LENGTH: 2897
<212> TYPE: DNA
<213> ORGANISM: Homo sapiens
<220> FEATURE:
<221> NAME/KEY: modified_base
<222> LOCATION: (2376)
<223> OTHER INFORMATION: n = a, t, c or g
<220> FEATURE:
<221> NAME/KEY: modified_base
<222> LOCATION: (2381)
<223> OTHER INFORMATION: n = a, t, c or g
<220> FEATURE:
<221> NAME/KEY: modified_base
<222> LOCATION: (2859)
<223> OTHER INFORMATION: n = a, t, c or g
<220> FEATURE:
<221> NAME/KEY: modified_base
<222> LOCATION: (2861)
<223> OTHER INFORMATION: n = a, t, c or g
```

```
<220> FEATURE:
<221> NAME/KEY: modified_base
<222> LOCATION: (2871)
<223> OTHER INFORMATION: n = a, t, c or g
<220> FEATURE:
<221> NAME/KEY: modified_base
<222> LOCATION: (2877)
<223> OTHER INFORMATION: n = a, t, c or g
<220> FEATURE:
<221> NAME/KEY: modified_base
<222> LOCATION: (2880)
<223> OTHER INFORMATION: n = a, t, c or g

<400> SEQUENCE: 1
```

| | | | | | |
|---|---|---|---|---|---|
| ggagagacat | gcgattggtg | accgagccga | gcggaccgaa | ggcgcgcccg | agatgcaggt | 60 |
| gagcaagagg | atgctggcgg | ggggcgtgag | gagcatgccc | agcccctcc | tggcctgctg | 120 |
| gcagcccatc | ctcctgctgg | tgctgggctc | agtgctgtca | ggctcggcca | cgggctgccc | 180 |
| gccccgctgc | gagtgctccg | cccaggaccg | cgctgtgctg | tgccaccgca | agcgctttgt | 240 |
| ggcagtcccc | gagggcatcc | ccaccgagac | gcgcctgctg | gacctaggca | agaaccgcat | 300 |
| caaaacgctc | aaccaggacg | agttcgccag | cttcccgcac | ctggaggagc | tggagctcaa | 360 |
| cgagaacatc | gtgagcgccg | tggagcccgg | cgccttcaac | aacctcttca | acctccggac | 420 |
| gctgggtctc | cgcagcaacc | gcctgaagct | catcccgcta | ggcgtcttca | ctggcctcag | 480 |
| caacctgacc | aagctggaca | tcagcgagaa | caagattgtt | atcctactgg | actacatgtt | 540 |
| tcaggacctg | tacaacctca | gtcactgga | ggttggcgac | aatgacctcg | tctacatctc | 600 |
| tcaccgcgcg | ttcagcggcc | tcaacagcct | ggagcagctg | acgctggaga | atgcaacct | 660 |
| gacctccatc | cccaccgagg | cgctgtccca | cctgcacggc | ctcatcgtcc | tgaggctccg | 720 |
| gcacctcaac | atcaatgcca | tccgggacta | ctccttcaag | aggctctacc | gactcaaggt | 780 |
| cttggagatc | tcccactggc | cctacttgga | caccatgaca | cccaactgcc | tctacggcct | 840 |
| caacctgacg | tccctgtcca | tcacacactg | caatctgacc | gctgtgccct | acctggccgt | 900 |
| ccgccaccta | gtctatctcc | gcttcctcaa | cctctcctac | aaccccatca | gcaccattga | 960 |
| gggctccatg | ttgcatgagc | tgctccggct | gcaggagatc | cagctggtgg | gcgggcagct | 1020 |
| ggccgtggtg | gagccctatg | ccttccgcgg | cctcaactac | ctgcgcgtgc | tcaatgtctc | 1080 |
| tggcaaccag | ctgaccacac | tggaggaatc | agtcttccac | tcggtgggca | acctggagac | 1140 |
| actcatcctg | gactccaacc | cgctggcctg | cgactgtcgg | ctcctgtggg | tgttccggcg | 1200 |
| ccgctggcgg | ctcaacttca | accggcagca | gcccacgtgc | gccacgcccg | agtttgtcca | 1260 |
| gggcaaggag | ttcaaggact | cccctgatgt | gctactgccc | aactacttca | cctgccgccg | 1320 |
| cgcccgcatc | cgggaccgca | aggcccagca | ggtgtttgtg | gacagggcc | acacggtgca | 1380 |
| gtttgtgtgc | cgggccgatg | gcgacccgcc | gcccgccatc | ctctggctct | caccccgaaa | 1440 |
| gcacctggtc | tcagccaaga | gcaatgggcg | gctcacagtc | ttccctgatg | gcacgctgga | 1500 |
| ggtgcgctac | gcccaggtac | aggacaacgg | cacgtacctg | tgcatcgcgg | ccaacgcggg | 1560 |
| cggcaacgac | tccatgcccg | cccacctgca | tgtgcgcagc | tactcgcccg | actggcccca | 1620 |
| tcagcccaac | aagaccttcg | ctttcatctc | caaccagccg | ggcgagggag | aggccaacag | 1680 |
| cacccgcgcc | actgtgcctt | tccccttcga | catcaagacc | ctcatcatcg | ccaccaccat | 1740 |
| gggcttcatc | tctttcctgg | gcgtcgtcct | cttctgcctg | gtgctgctgt | ttctctggag | 1800 |
| ccggggcaag | gcaacacaa | agcacaacat | cgagatcgag | tatgtgcccc | gaaagtcgga | 1860 |
| cgcaggcatc | agctccgccg | acgcgccccg | caagttcaac | atgaagatga | tatgaggccg | 1920 |
| gggcggggg | cagggacccc | cggcggccg | ggcaggggaa | ggggcctggc | cgccacctgc | 1980 |

-continued

```
tcactctcca gtccttccca cctcctccct accttctac acacgttctc tttctccctc    2040
ccgcctccgt cccctgctgc ccccgccag ccctcaccac ctgccctcct tctaccagga    2100
cctcagaagc ccagacctgg ggaccccacc tacacagggg cattgacaga ctggagttga    2160
aagccgacga accgacacgc ggcagagtca ataattcaat aaaaaagtta cgaactttct    2220
ctgtaacttg ggtttcaata attatggatt tttatgaaaa cttgaaataa taaaaagaga    2280
aaaaaactat ttcctatagc tagtcggaat gcaaactttt gacgtcctga ttgctccagg    2340
gccctcttcc aactcagttt cttgtttttc tcttcntcct nctcctcttc ttcctccttt    2400
ctcttctctt cccccagtgg ggagggatca ctcaggaaaa caggaaagga ggttccagcc    2460
ccacccacct gcccaccccg ccccaggcac catcaggagc aggctagggg gcaggcctgg    2520
gcccagctcc gggctggctt tttgcagggc gcaggtggag gggacaggtc tgccgatggg    2580
ggtgggagcc tgtctgctgg gctgccaggc ggcaccactg caagggtgg gagcctggct    2640 cgggtgtggc tgagactctg gacagaggct ggggtcctcc tggggacag cacagtcagt    2700 ggagagagcc aggggctgga ggtggggccc accccagcct ctggtcccag ctctgctgct    2760
cacttgctgt gtggccctca agcaggtcca ctggcctctc tgggcctcag tctccacatc    2820
tgtacaaatg ggaacattac cccctgccct gcctacctna nagggctgtt ntgaggnatn    2880
gatgagatga tgtatgt                                                   2897
```

```
<210> SEQ ID NO 2
<211> LENGTH: 614
<212> TYPE: PRT
<213> ORGANISM: Homo sapiens

<400> SEQUENCE: 2

Met Leu Ala Gly Gly Val Arg Ser Met Pro Ser Pro Leu Leu Ala Cys
  1               5                  10                  15

Trp Gln Pro Ile Leu Leu Leu Val Leu Gly Ser Val Leu Ser Gly Ser
             20                  25                  30

Ala Thr Gly Cys Pro Pro Arg Cys Glu Cys Ser Ala Gln Asp Arg Ala
         35                  40                  45

Val Leu Cys His Arg Lys Arg Phe Val Ala Val Pro Glu Gly Ile Pro
     50                  55                  60

Thr Glu Thr Arg Leu Leu Asp Leu Gly Lys Asn Arg Ile Lys Thr Leu
 65                  70                  75                  80

Asn Gln Asp Glu Phe Ala Ser Phe Pro His Leu Glu Glu Leu Glu Leu
                 85                  90                  95

Asn Glu Asn Ile Val Ser Ala Val Glu Pro Gly Ala Phe Asn Asn Leu
            100                 105                 110

Phe Asn Leu Arg Thr Leu Gly Leu Arg Ser Asn Arg Leu Lys Leu Ile
        115                 120                 125

Pro Leu Gly Val Phe Thr Gly Leu Ser Asn Leu Thr Lys Leu Asp Ile
    130                 135                 140

Ser Glu Asn Lys Ile Val Ile Leu Leu Asp Tyr Met Phe Gln Asp Leu
145                 150                 155                 160

Tyr Asn Leu Lys Ser Leu Glu Val Gly Asp Asn Asp Leu Val Tyr Ile
                165                 170                 175

Ser His Arg Ala Phe Ser Gly Leu Asn Ser Leu Glu Gln Leu Thr Leu
            180                 185                 190

Glu Lys Cys Asn Leu Thr Ser Ile Pro Thr Glu Ala Leu Ser His Leu
        195                 200                 205
```

-continued

```
His Gly Leu Ile Val Leu Arg Leu Arg His Leu Asn Ile Asn Ala Ile
    210                 215                 220

Arg Asp Tyr Ser Phe Lys Arg Leu Tyr Arg Leu Lys Val Leu Glu Ile
225                 230                 235                 240

Ser His Trp Pro Tyr Leu Asp Thr Met Thr Pro Asn Cys Leu Tyr Gly
                245                 250                 255

Leu Asn Leu Thr Ser Leu Ser Ile Thr His Cys Asn Leu Thr Ala Val
            260                 265                 270

Pro Tyr Leu Ala Val Arg His Leu Val Tyr Leu Arg Phe Leu Asn Leu
        275                 280                 285

Ser Tyr Asn Pro Ile Ser Thr Ile Glu Gly Ser Met Leu His Glu Leu
290                 295                 300

Leu Arg Leu Gln Glu Ile Gln Leu Val Gly Gly Gln Leu Ala Val Val
305                 310                 315                 320

Glu Pro Tyr Ala Phe Arg Gly Leu Asn Tyr Leu Arg Val Leu Asn Val
                325                 330                 335

Ser Gly Asn Gln Leu Thr Thr Leu Glu Glu Ser Val Phe His Ser Val
            340                 345                 350

Gly Asn Leu Glu Thr Leu Ile Leu Asp Ser Asn Pro Leu Ala Cys Asp
        355                 360                 365

Cys Arg Leu Leu Trp Val Phe Arg Arg Arg Trp Arg Leu Asn Phe Asn
370                 375                 380

Arg Gln Gln Pro Thr Cys Ala Thr Pro Glu Phe Val Gln Gly Lys Glu
385                 390                 395                 400

Phe Lys Asp Phe Pro Asp Val Leu Leu Pro Asn Tyr Phe Thr Cys Arg
                405                 410                 415

Arg Ala Arg Ile Arg Asp Arg Lys Ala Gln Gln Val Phe Val Asp Glu
            420                 425                 430

Gly His Thr Val Gln Phe Val Cys Arg Ala Asp Gly Asp Pro Pro Pro
        435                 440                 445

Ala Ile Leu Trp Leu Ser Pro Arg Lys His Leu Val Ser Ala Lys Ser
450                 455                 460

Asn Gly Arg Leu Thr Val Phe Pro Asp Gly Thr Leu Glu Val Arg Tyr
465                 470                 475                 480

Ala Gln Val Gln Asp Asn Gly Thr Tyr Leu Cys Ile Ala Ala Asn Ala
                485                 490                 495

Gly Gly Asn Asp Ser Met Pro Ala His Leu His Val Arg Ser Tyr Ser
            500                 505                 510

Pro Asp Trp Pro His Gln Pro Asn Lys Thr Phe Ala Phe Ile Ser Asn
        515                 520                 525

Gln Pro Gly Glu Gly Glu Ala Asn Ser Thr Arg Ala Thr Val Pro Phe
530                 535                 540

Pro Phe Asp Ile Lys Thr Leu Ile Ile Ala Thr Thr Met Gly Phe Ile
545                 550                 555                 560

Ser Phe Leu Gly Val Val Leu Phe Cys Leu Val Leu Leu Phe Leu Trp
                565                 570                 575

Ser Arg Gly Lys Gly Asn Thr Lys His Asn Ile Glu Ile Glu Tyr Val
            580                 585                 590

Pro Arg Lys Ser Asp Ala Gly Ile Ser Ser Ala Asp Ala Pro Arg Lys
        595                 600                 605

Phe Asn Met Lys Met Ile
    610
```

<210> SEQ ID NO 3
<211> LENGTH: 59
<212> TYPE: DNA
<213> ORGANISM: Artificial Sequence
<220> FEATURE:
<223> OTHER INFORMATION: Description of Artificial Sequence: Primer

<400> SEQUENCE: 3
tcgagaaaaa agatcgtcat cctgctagac tctcttgaag tctagcagga tgacgatca        59

<210> SEQ ID NO 4
<211> LENGTH: 9
<212> TYPE: PRT
<213> ORGANISM: Homo sapiens

<400> SEQUENCE: 4

Arg Arg Ala Arg Ile Arg Asp Arg Lys
  1               5

<210> SEQ ID NO 5
<211> LENGTH: 9
<212> TYPE: PRT
<213> ORGANISM: Homo sapiens

<400> SEQUENCE: 5

Lys Lys Val Lys Val Lys Glu Lys Arg
  1               5

<210> SEQ ID NO 6
<211> LENGTH: 9
<212> TYPE: PRT
<213> ORGANISM: Homo sapiens

<400> SEQUENCE: 6

Arg Arg Leu Arg Leu Arg Asp Arg Lys
  1               5

<210> SEQ ID NO 7
<211> LENGTH: 9
<212> TYPE: PRT
<213> ORGANISM: Homo sapiens

<400> SEQUENCE: 7

Arg Arg Gly Arg Gly Arg Asp Arg Lys
  1               5

<210> SEQ ID NO 8
<211> LENGTH: 9
<212> TYPE: PRT
<213> ORGANISM: Homo sapiens

<400> SEQUENCE: 8

Arg Arg Ile Arg Ala Arg Asp Arg Lys
  1               5

<210> SEQ ID NO 9
<211> LENGTH: 6
<212> TYPE: PRT
<213> ORGANISM: Homo sapiens

<400> SEQUENCE: 9

Met Gln Val Ser Lys Arg
  1               5

```
<210> SEQ ID NO 10
<211> LENGTH: 6
<212> TYPE: PRT
<213> ORGANISM: Homo sapiens

<400> SEQUENCE: 10

Leu Ser Pro Arg Lys His
 1               5

<210> SEQ ID NO 11
<211> LENGTH: 6
<212> TYPE: PRT
<213> ORGANISM: Homo sapiens

<400> SEQUENCE: 11

Ile Thr Pro Lys Arg Arg
 1               5

<210> SEQ ID NO 12
<211> LENGTH: 6
<212> TYPE: PRT
<213> ORGANISM: Homo sapiens

<400> SEQUENCE: 12

Ala Cys Pro His His Lys
 1               5

<210> SEQ ID NO 13
<211> LENGTH: 6
<212> TYPE: PRT
<213> ORGANISM: Homo sapiens

<400> SEQUENCE: 13

Val Ser Pro Arg Lys His
 1               5

<210> SEQ ID NO 14
<211> LENGTH: 23
<212> TYPE: DNA
<213> ORGANISM: Artificial Sequence
<220> FEATURE:
<223> OTHER INFORMATION: Description of Artificial Sequence: Primer

<400> SEQUENCE: 14
aaggcccagc aggtgtttgt gga                                           23

<210> SEQ ID NO 15
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 15
tactcgatct cgatgttgtg cttt                                          24

<210> SEQ ID NO 16
<211> LENGTH: 37
<212> TYPE: DNA
<213> ORGANISM: Artificial Sequence
<220> FEATURE:
<223> OTHER INFORMATION: Description of Artificial Sequence: Primer

<400> SEQUENCE: 16
cagcaggtcg acgcggccgc atgctggcgg ggggcgt                            37
```

```
<210> SEQ ID NO 17
<211> LENGTH: 29
<212> TYPE: DNA
<213> ORGANISM: Homo sapiens

<400> SEQUENCE: 17
cagcaggtcg acctcgcccg gctggttgg                                    29

<210> SEQ ID NO 18
<211> LENGTH: 37
<212> TYPE: DNA
<213> ORGANISM: Artificial Sequence
<220> FEATURE:
<223> OTHER INFORMATION: Description of Artificial Sequence: Primer

<400> SEQUENCE: 18
aattaagaat tcacgggctg cccgccccgc tgcgagt                           37

<210> SEQ ID NO 19
<211> LENGTH: 44
<212> TYPE: DNA
<213> ORGANISM: Artificial Sequence
<220> FEATURE:
<223> OTHER INFORMATION: Description of Artificial Sequence: Primer

<400> SEQUENCE: 19
tatatttcta gatcactcgc ccggctggtt ggagatgaaa gcga                   44

<210> SEQ ID NO 20
<211> LENGTH: 44
<212> TYPE: DNA
<213> ORGANISM: Artificial Sequence
<220> FEATURE:
<223> OTHER INFORMATION: Description of Artificial Sequence: Primer

<400> SEQUENCE: 20
cttgacacgg gatccgcggc cgcatgctgg cggggggcgt gagg                   44

<210> SEQ ID NO 21
<211> LENGTH: 45
<212> TYPE: DNA
<213> ORGANISM: Artificial Sequence
<220> FEATURE:
<223> OTHER INFORMATION: Description of Artificial Sequence: Primer

<400> SEQUENCE: 21
gcagcggggc gggcagcccg tggccgagcc tgacagcact gagcc                  45

<210> SEQ ID NO 22
<211> LENGTH: 44
<212> TYPE: DNA
<213> ORGANISM: Artificial Sequence
<220> FEATURE:
<223> OTHER INFORMATION: Description of Artificial Sequence: Primer

<400> SEQUENCE: 22
cttgacacgg gatccgcggc cgcatgctgg cggggggcgt gagg                   44

<210> SEQ ID NO 23
<211> LENGTH: 45
<212> TYPE: DNA
<213> ORGANISM: Artificial Sequence
<220> FEATURE:
<223> OTHER INFORMATION: Description of Artificial Sequence: Primer

<400> SEQUENCE: 23
gtcccggatg cgggcgcggg ccgagcctga cagcactgag cccag                  45
```

```
<210> SEQ ID NO 24
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 24
atattctaga atgctggcgg ggggcgtgag                                    30

<210> SEQ ID NO 25
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 25
atatactagt gtcgttgccg cccgcgttgg                                    30

<210> SEQ ID NO 26
<211> LENGTH: 46
<212> TYPE: DNA
<213> ORGANISM: Artificial Sequence
<220> FEATURE:
<223> OTHER INFORMATION: Description of Artificial Sequence: Primer

<400> SEQUENCE: 26
cccagcaggt gtttgtggac gagtgatcta gggccgcgga tccctg                  46

<210> SEQ ID NO 27
<211> LENGTH: 46
<212> TYPE: DNA
<213> ORGANISM: Artificial Sequence
<220> FEATURE:
<223> OTHER INFORMATION: Description of Artificial Sequence: Primer

<400> SEQUENCE: 27
cagggatccg cggccctaga tcactcgtcc acaaacacct gctggg                  46

<210> SEQ ID NO 28
<211> LENGTH: 43
<212> TYPE: DNA
<213> ORGANISM: Artificial Sequence
<220> FEATURE:
<223> OTHER INFORMATION: Description of Artificial Sequence: Primer

<400> SEQUENCE: 28
cgccgcgcac ccgggtgaat tccgcgcccg catccgggac cgc                     43

<210> SEQ ID NO 29
<211> LENGTH: 43
<212> TYPE: DNA
<213> ORGANISM: Artificial Sequence
<220> FEATURE:
<223> OTHER INFORMATION: Description of Artificial Sequence: Primer

<400> SEQUENCE: 29
gcggtcccgg atgcgggcgc ggaattcacc cgggtgcgcg gcg                     43

<210> SEQ ID NO 30
<211> LENGTH: 43
<212> TYPE: DNA
<213> ORGANISM: Artificial Sequence
<220> FEATURE:
<223> OTHER INFORMATION: Description of Artificial Sequence: Primer
```

-continued

<400> SEQUENCE: 30
cgccgcgcac ccgggtgaat tcgcccagca ggtgtttgtg gac                43

<210> SEQ ID NO 31
<211> LENGTH: 43
<212> TYPE: DNA
<213> ORGANISM: Artificial Sequence
<220> FEATURE:
<223> OTHER INFORMATION: Description of Artificial Sequence: Primer

<400> SEQUENCE: 31
gtccacaaac acctgctggg cgaattcacc cgggtgcgcg gcg                43

<210> SEQ ID NO 32
<211> LENGTH: 46
<212> TYPE: DNA
<213> ORGANISM: Artificial Sequence
<220> FEATURE:
<223> OTHER INFORMATION: Description of Artificial Sequence: Primer

<400> SEQUENCE: 32
catcctctgg ctctcacccg aaaaggtact ggtctcagcc aagagc             46

<210> SEQ ID NO 33
<211> LENGTH: 46
<212> TYPE: DNA
<213> ORGANISM: Artificial Sequence
<220> FEATURE:
<223> OTHER INFORMATION: Description of Artificial Sequence: Primer

<400> SEQUENCE: 33
gctcttggct gagaccagta cctttttcggg tgagagccag aggatg            46

<210> SEQ ID NO 34
<211> LENGTH: 5
<212> TYPE: PRT
<213> ORGANISM: Homo sapiens

<400> SEQUENCE: 34

Ser Pro Arg Lys His
 1               5

<210> SEQ ID NO 35
<211> LENGTH: 31
<212> TYPE: DNA
<213> ORGANISM: Artificial Sequence
<220> FEATURE:
<223> OTHER INFORMATION: Description of Artificial Sequence: Primer

<400> SEQUENCE: 35
aattaagcgg ccgcatgctg gcggggggcg t                             31

<210> SEQ ID NO 36
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 36
aattaagcgg ccgctttgtc atgt                                     24

<210> SEQ ID NO 37
<211> LENGTH: 32
<212> TYPE: DNA
<213> ORGANISM: Artificial Sequence

```
<220> FEATURE:
<223> OTHER INFORMATION: Description of Artificial Sequence: Primer

<400> SEQUENCE: 37
gattactcga gatgctggcg gggggcgtga gg                                    32

<210> SEQ ID NO 38
<211> LENGTH: 36
<212> TYPE: DNA
<213> ORGANISM: Artificial Sequence
<220> FEATURE:
<223> OTHER INFORMATION: Description of Artificial Sequence: Primer

<400> SEQUENCE: 38
cgcgggaatt ctcatatcat cttcatgttg aacttg                                36

<210> SEQ ID NO 39
<211> LENGTH: 33
<212> TYPE: DNA
<213> ORGANISM: Artificial Sequence
<220> FEATURE:
<223> OTHER INFORMATION: Description of Artificial Sequence: Primer

<400> SEQUENCE: 39
gccttccgcg gcctcaacta cctgcgcgtg ctc                                   33

<210> SEQ ID NO 40
<211> LENGTH: 75
<212> TYPE: DNA
<213> ORGANISM: Artificial Sequence
<220> FEATURE:
<223> OTHER INFORMATION: Description of Artificial Sequence: Primer

<400> SEQUENCE: 40
ccggaattct caagcgtaat caggaacgtc gtaagggtat atcatcttca tgttgaactt      60
gcggggcgcg tcggc                                                       75

<210> SEQ ID NO 41
<211> LENGTH: 55
<212> TYPE: DNA
<213> ORGANISM: Artificial Sequence
<220> FEATURE:
<223> OTHER INFORMATION: Description of Artificial Sequence: Primer

<400> SEQUENCE: 41
tgatcgtcat cctgctagac ttcaagagag tctagcagga tgacgatctt ttttc           55
```